United States Patent
McNiven et al.

(10) Patent No.: US 8,221,112 B2
(45) Date of Patent: *Jul. 17, 2012

(54) METHOD FOR RETAINING A VASCULAR STENT ON A CATHETER

(75) Inventors: Sean McNiven, Del Mar, CA (US); Jonathan Durcan, Temecula, CA (US); Boyd V. Knott, Menifee, CA (US); Jeremy Stigall, Murrieta, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/091,847

(22) Filed: Apr. 21, 2011

(65) Prior Publication Data

US 2011/0203739 A1 Aug. 25, 2011

Related U.S. Application Data

(60) Division of application No. 11/521,993, filed on Sep. 15, 2006, now Pat. No. 7,947,207, which is a continuation-in-part of application No. 11/453,747, filed on Jun. 15, 2006, now Pat. No. 7,763,198, which is a continuation-in-part of application No. 11/105,085, filed on Apr. 12, 2005, now Pat. No. 7,563,400.

(51) Int. Cl.
  *B29C 33/02* (2006.01)
(52) U.S. Cl. ......... 425/522; 249/111; 249/170; 425/470
(58) Field of Classification Search .................. 249/111, 249/170; 425/522, 470
  See application file for complete search history.

(56) References Cited

U.S. PATENT DOCUMENTS

| | | |
|---|---|---|
| 141,992 A | 8/1873 | Carr |
| 430,928 A | 6/1890 | Doty |
| 579,214 A | 3/1897 | Adams |
| 696,289 A | 2/1902 | Williams |
| 852,290 A | 4/1907 | Neal |
| 915,184 A | 3/1909 | Keirn |
| 1,045,886 A | 12/1912 | Reay |
| 1,230,561 A | 6/1917 | Chige |
| 1,268,171 A | 6/1918 | Spaulding |

(Continued)

FOREIGN PATENT DOCUMENTS

AU 23784/88 A 4/1989

(Continued)

OTHER PUBLICATIONS

Office Action dated Jul. 22, 2011 in the co-pending Japanese Application No. 2008-506676.

(Continued)

*Primary Examiner* — Robert B Davis
(74) *Attorney, Agent, or Firm* — Fulwider Patton LLP

(57) ABSTRACT

A method of securely mounting a stent on a balloon of a catheter. The method generally includes crimping a stent on a balloon of a catheter at least one time, and positioning the balloon with the stent thereon within a polished bore of a mold formed at least in part of a metallic material. The balloon is pressurized and heated within the mold, or within a sheath, in two stages as the stent is restrained from radially expanding. The method may include crimping the stent onto the balloon one or two times during processing. The method increases retention of the stent on the balloon catheter following sterilization.

21 Claims, 6 Drawing Sheets

U.S. PATENT DOCUMENTS

| | | |
|---|---|---|
| 1,493,515 A | 5/1924 | Berthold |
| 1,758,261 A | 5/1930 | Leland |
| 2,079,498 A | 5/1937 | Douglas |
| 2,452,857 A | 11/1948 | Mesaros |
| 2,465,433 A | 3/1949 | Doniger |
| 2,553,479 A | 5/1951 | Schmarje et al. |
| 2,701,559 A | 2/1955 | Cooper |
| 2,964,088 A | 12/1960 | Erath |
| 3,105,492 A | 10/1963 | Jeckel |
| 3,203,078 A | 8/1965 | Ustin |
| 3,164,042 A | 11/1967 | Hanna et al. |
| 3,350,908 A | 11/1967 | Andrews et al. |
| 3,439,519 A | 4/1969 | Gerding |
| 3,496,684 A | 2/1970 | Banning et al. |
| 3,568,495 A | 3/1971 | Duffield et al. |
| 3,619,885 A | 11/1971 | Dischler |
| 3,657,744 A | 4/1972 | Ersek |
| 3,868,956 A | 3/1975 | Alfidi et al. |
| 3,898,987 A | 8/1975 | Elam |
| 3,993,078 A | 11/1976 | Bergentz et al. |
| 4,043,172 A | 8/1977 | Schmittou |
| 4,070,745 A | 1/1978 | Schimmelman |
| 4,107,964 A | 8/1978 | Smith |
| 4,130,904 A | 12/1978 | Whalen |
| 4,140,126 A | 2/1979 | Choudhury |
| 4,159,719 A | 7/1979 | Haerr |
| 4,215,871 A | 8/1980 | Hirsch et al. |
| 4,241,146 A | 12/1980 | Sivachenko et al. |
| 4,323,071 A | 4/1982 | Simpson et al. |
| 4,353,240 A | 10/1982 | Undin et al. |
| 4,373,923 A | 2/1983 | Kilwin |
| 4,379,397 A | 4/1983 | Langr |
| 4,387,952 A | 6/1983 | Slusher |
| 4,454,657 A | 6/1984 | Yasumi |
| 4,455,854 A | 6/1984 | Ermolovich et al. |
| 4,468,224 A | 8/1984 | Enzmann et al. |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,576,142 A | 3/1986 | Schiff |
| 4,580,568 A | 4/1986 | Gianturco |
| 4,606,347 A | 8/1986 | Fogarty et al. |
| 4,614,107 A | 9/1986 | Norin |
| 4,616,652 A | 10/1986 | Simpson |
| 4,619,246 A | 10/1986 | Molgaard-Nielsen et al. |
| 4,644,936 A | 2/1987 | Schiff |
| 4,649,922 A | 3/1987 | Wiktor |
| 4,650,466 A | 3/1987 | Luther |
| 4,655,771 A | 4/1987 | Wallsten |
| 4,665,906 A | 5/1987 | Jervis |
| 4,665,918 A | 5/1987 | Garza et al. |
| 4,681,092 A | 7/1987 | Cho et al. |
| 4,681,110 A | 7/1987 | Wiktor |
| 4,697,573 A | 10/1987 | Schiff |
| 4,703,546 A | 11/1987 | Gilbert |
| 4,706,671 A | 11/1987 | Weinrib |
| 4,725,334 A | 2/1988 | Brimm |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininter |
| 4,768,507 A | 9/1988 | Fischell et al. |
| 4,776,337 A | 10/1988 | Palmaz |
| 4,786,271 A | 11/1988 | Menn |
| 4,795,458 A | 1/1989 | Regan |
| 4,800,882 A | 1/1989 | Gianturco |
| 4,830,003 A | 5/1989 | Wolff et al. |
| 4,838,264 A | 6/1989 | Bremer et al. |
| 4,848,343 A | 7/1989 | Wallsten et al. |
| 4,856,516 A | 8/1989 | Hillstead |
| 4,864,924 A | 9/1989 | Storace |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,901,707 A | 2/1990 | Schiff |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,961,291 A | 10/1990 | Lagasee |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,987,722 A | 1/1991 | Koebbeman |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,067,957 A | 11/1991 | Jervis |
| 5,071,407 A | 12/1991 | Termin et al. |
| 5,073,694 A | 12/1991 | Tessier et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,132,066 A | 7/1992 | Charlesworth et al. |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,189,786 A | 3/1993 | Ishikawa et al. |
| 5,192,297 A | 3/1993 | Hull |
| 5,192,307 A | 3/1993 | Wall |
| 5,192,311 A | 3/1993 | King et al. |
| 5,195,539 A | 3/1993 | Dyrud et al. |
| 5,195,984 A | 3/1993 | Schatz |
| 5,197,978 A | 3/1993 | Hess |
| 5,207,960 A | 5/1993 | Moret de Rocheprise |

| | | | | | | |
|---|---|---|---|---|---|---|
| 5,209,143 A | 5/1993 | Sweet | | 5,727,411 A | 3/1998 | Sakakibara et al. |
| 5,209,799 A | 5/1993 | Vigil | | 5,733,303 A | 3/1998 | Israel |
| 5,216,263 A | 6/1993 | Paoli | | 5,733,325 A | 3/1998 | Robinson |
| 5,217,434 A | 6/1993 | Arney | | 5,738,674 A | 4/1998 | Williams et al. |
| 5,217,482 A | 6/1993 | Keith | | 5,741,327 A | 4/1998 | Frantzen |
| 5,222,971 A | 6/1993 | Willard et al. | | 5,746,764 A | 5/1998 | Green et al. |
| 5,226,913 A | 7/1993 | Pinchuk | | 5,746,765 A | 5/1998 | Kleshinski et al. |
| 5,234,456 A | 8/1993 | Silvestrini | | 5,759,474 A | 6/1998 | Rupp et al. |
| 5,242,397 A | 9/1993 | Barath et al. | | 5,776,161 A | 7/1998 | Globerman |
| 5,242,399 A | 9/1993 | Lau et al. | | 5,782,855 A | 7/1998 | Lau et al. |
| 5,242,452 A | 9/1993 | Inoue | | 5,782,903 A | 7/1998 | Wiktor |
| 5,254,091 A * | 10/1993 | Aliahmad et al. ....... 604/103.06 | | 5,783,227 A | 7/1998 | Dunham |
| 5,263,969 A | 11/1993 | Phillips | | 5,785,715 A | 7/1998 | Schatz |
| 5,282,823 A | 2/1994 | Schwartz et al. | | 5,787,572 A | 8/1998 | Toms et al. |
| 5,282,824 A | 2/1994 | Gianturco | | 5,795,289 A | 8/1998 | Wyttenbach |
| 5,290,295 A | 3/1994 | Querals et al. | | 5,800,521 A | 9/1998 | Orth |
| 5,290,305 A | 3/1994 | Inoue | | 5,800,526 A | 9/1998 | Anderson et al. |
| 5,292,331 A | 3/1994 | Boneau | | 5,810,838 A | 9/1998 | Solar |
| 5,304,200 A | 4/1994 | Spaulding | | 5,810,868 A | 9/1998 | Lashinski et al. |
| 5,306,377 A * | 4/1994 | Jensen et al. ............... 156/304.2 | | 5,810,871 A | 9/1998 | Tuckey et al. |
| 5,314,444 A | 5/1994 | Gianturco | | 5,810,873 A | 9/1998 | Morales |
| 5,314,472 A | 5/1994 | Fontaine | | 5,817,152 A | 10/1998 | Birdsall |
| 5,329,797 A | 7/1994 | Calhoun | | 5,827,321 A | 10/1998 | Roubin et al. |
| 5,330,500 A | 7/1994 | Song | | 5,830,217 A | 11/1998 | Ryan |
| 5,336,234 A | 8/1994 | Vigil et al. | | 5,836,952 A | 11/1998 | Davis et al. |
| 5,344,425 A | 9/1994 | Sawyer | | 5,836,965 A | 11/1998 | Jendersee et al. |
| 5,344,426 A | 9/1994 | Lau et al. | | 5,836,966 A | 11/1998 | St. Germain |
| 5,352,197 A | 10/1994 | Hammersmark et al. | | 5,855,600 A | 1/1999 | Alt |
| 5,354,308 A | 10/1994 | Simon et al. | | 5,860,966 A | 1/1999 | Tower |
| 5,356,433 A | 10/1994 | Rowland et al. | | 5,861,027 A | 1/1999 | Trap |
| 5,360,401 A | 11/1994 | Turnlund | | 5,893,852 A | 4/1999 | Morales |
| 5,368,566 A | 11/1994 | Crocker | | 5,893,867 A | 4/1999 | Bagaoisan et al. |
| 5,372,600 A | 12/1994 | Beyar et al. | | 5,902,332 A | 5/1999 | Schatz |
| 5,378,239 A | 1/1995 | Termin et al. | | 5,906,640 A | 5/1999 | Penn et al. |
| 5,383,892 A | 1/1995 | Cardon et al. | | 5,911,452 A | 6/1999 | Yan |
| 5,395,390 A | 3/1995 | Simon et al. | | 5,911,754 A | 6/1999 | Kanesaka et al. |
| 5,405,378 A | 4/1995 | Strecker | | 5,920,975 A | 7/1999 | Morales |
| 5,413,597 A | 5/1995 | Krajicek | | 5,922,021 A | 7/1999 | Jang |
| 5,421,955 A | 6/1995 | Lau | | 5,925,061 A | 7/1999 | Ogi et al. |
| 5,423,745 A | 6/1995 | Todd et al. | | 5,931,851 A | 8/1999 | Morales |
| 5,423,885 A | 6/1995 | Williams | | 5,938,696 A | 8/1999 | Goicoechea et al. |
| 5,437,083 A | 8/1995 | Williams et al. | | 5,938,697 A | 8/1999 | Killion et al. |
| 5,445,646 A | 8/1995 | Euteneuer et al. | | 5,944,735 A | 8/1999 | Green et al. |
| 5,449,373 A | 9/1995 | Pinchasik | | 5,947,993 A | 9/1999 | Morales |
| 5,456,667 A | 10/1995 | Ham et al. | | 5,948,016 A | 9/1999 | Jang |
| 5,456,694 A | 10/1995 | Marin et al. | | 5,948,191 A | 9/1999 | Solovay |
| 5,458,615 A | 10/1995 | Klemm et al. | | 5,951,569 A | 9/1999 | Tuckey et al. |
| 5,465,716 A | 11/1995 | Avitall | | 5,954,743 A | 9/1999 | Jang |
| 5,476,476 A | 12/1995 | Hillstead | | 5,972,016 A | 10/1999 | Morales |
| 5,476,505 A | 12/1995 | Limon | | 5,974,652 A | 11/1999 | Kimes et al. |
| 5,476,506 A | 12/1995 | Lunn | | 5,980,552 A | 11/1999 | Pinchasik et al. |
| 5,481,893 A | 1/1996 | Barjasteh et al. | | 5,984,964 A | 11/1999 | Roberts et al. |
| 5,484,449 A | 1/1996 | Amundson et al. | | 5,997,468 A | 12/1999 | Wolff et al. |
| 5,507,768 A | 4/1996 | Lau et al. | | 6,009,614 A | 1/2000 | Morales |
| 5,514,154 A | 5/1996 | Lau et al. | | 6,010,530 A | 1/2000 | Goicoechea |
| 5,527,324 A | 6/1996 | Krantz et al. | | 6,017,365 A | 1/2000 | Von Oepen |
| 5,540,124 A | 7/1996 | Srhoj | | 6,024,737 A | 2/2000 | Morales |
| 5,545,132 A | 8/1996 | Fagan et al. | | 6,030,413 A | 2/2000 | Lazarus |
| 5,546,646 A | 8/1996 | Williams et al. | | 6,033,435 A | 3/2000 | Penn et al. |
| 5,569,295 A | 10/1996 | Lam | | 6,042,597 A | 3/2000 | Kveen et al. |
| 5,571,135 A | 11/1996 | Fraser et al. | | 6,042,606 A | 3/2000 | Frantzen |
| 5,603,721 A | 2/1997 | Lau et al. | | 6,048,361 A | 4/2000 | Von Oepen |
| 5,626,474 A | 5/1997 | Kukla et al. | | 6,051,002 A | 4/2000 | Morales |
| 5,626,604 A | 5/1997 | Cottone et al. | | 6,059,822 A | 5/2000 | Kanesaka et al. |
| 5,628,754 A | 5/1997 | Shevlin et al. | | 6,063,092 A | 5/2000 | Shin |
| 5,630,830 A | 5/1997 | Verbeek | | 6,063,102 A | 5/2000 | Morales |
| 5,653,690 A | 8/1997 | Booth et al. | | 6,066,168 A | 5/2000 | Lau et al. |
| 5,653,691 A | 8/1997 | Rupp et al. | | 6,071,298 A | 6/2000 | Lashinski et al. |
| 5,653,727 A | 8/1997 | Wiktor | | 6,071,308 A | 6/2000 | Ballou et al. |
| 5,658,181 A | 8/1997 | Brown, II | | 6,082,990 A | 7/2000 | Jackson et al. |
| 5,672,169 A | 9/1997 | Verbeek | | 6,092,273 A | 7/2000 | Villareal |
| 5,693,066 A | 12/1997 | Rupp et al. | | 6,106,548 A | 8/2000 | Roubin et al. |
| 5,693,089 A | 12/1997 | Inoue | | 6,108,886 A | 8/2000 | Kimes et al. |
| 5,695,515 A | 12/1997 | Orejola | | 6,125,523 A | 10/2000 | Brown et al. |
| 5,715,723 A | 2/1998 | Owens | | 6,141,855 A | 11/2000 | Morales |
| 5,716,393 A | 2/1998 | Lindenberg et al. | | 6,146,358 A | 11/2000 | Rowe |
| 5,716,396 A | 2/1998 | Williams | | 6,146,403 A | 11/2000 | St. Germain |
| 5,720,726 A | 2/1998 | Marcadis et al. | | 6,159,238 A | 12/2000 | Killion et al. |
| 5,725,519 A | 3/1998 | Penner et al. | | 6,167,605 B1 | 1/2001 | Morales |

| | | | | | | |
|---|---|---|---|---|---|---|
| 6,176,116 B1 | 1/2001 | Wilhelm et al. | EP | 0308512 A1 | 3/1989 | |
| 6,179,867 B1 | 1/2001 | Cox | EP | 0312852 A1 | 4/1989 | |
| 6,183,506 B1 | 2/2001 | Penn et al. | EP | 0 338 816 A2 | 10/1989 | |
| 6,200,337 B1 | 3/2001 | Moriuchi et al. | EP | 0335341 A1 | 10/1989 | |
| 6,202,272 B1 | 3/2001 | Jackson | EP | 0338816 A2 | 10/1989 | |
| 6,206,910 B1 | 3/2001 | Berry et al. | EP | 0357003 A2 | 3/1990 | |
| 6,217,608 B1 | 4/2001 | Penn et al. | EP | 0 361 192 A3 | 4/1990 | |
| 6,231,598 B1 | 5/2001 | Berry et al. | EP | 0 364 787 A1 | 4/1990 | |
| 6,273,901 B1 | 8/2001 | Whitcher et al. | EP | 0361192 A2 | 4/1990 | |
| 6,273,910 B1 | 8/2001 | Limon | EP | 0364787 A1 | 4/1990 | |
| 6,273,911 B1 | 8/2001 | Cox | EP | 0 372 789 A3 | 6/1990 | |
| 6,287,336 B1 | 9/2001 | Globerman et al. | EP | 0372789 A2 | 6/1990 | |
| 6,293,959 B1 | 9/2001 | Miller et al. | EP | 0380668 A1 | 8/1990 | |
| 6,340,366 B2 | 1/2002 | Wijay | EP | 0407951 A2 | 8/1990 | |
| 6,344,055 B1 | 2/2002 | Shukov | EP | 0 407 951 A3 | 1/1991 | |
| 6,458,313 B2 * | 10/2002 | Hudgins et al. ............... 264/515 | EP | 0 408 245 A1 | 1/1991 | |
| 6,510,722 B1 | 1/2003 | Ching et al. | EP | 0408245 A1 | 1/1991 | |
| 6,571,719 B2 | 6/2003 | MacDonald | EP | 0417928 B1 | 3/1991 | |
| 6,749,419 B2 * | 6/2004 | Nightingale et al. ......... 425/532 | EP | 0 421 729 A2 | 4/1991 | |
| 6,823,576 B2 | 11/2004 | Austin | EP | 0 423 916 A1 | 4/1991 | |
| 6,863,683 B2 | 3/2005 | Schwager et al. | EP | 0421729 A2 | 4/1991 | |
| 6,875,197 B1 * | 4/2005 | Simhambhatla et al. .. 604/96.01 | EP | 0 428 479 A1 | 5/1991 | |
| 6,881,216 B2 | 4/2005 | Di Caprio et al. | EP | 0428471 A2 | 5/1991 | |
| 6,915,560 B2 | 7/2005 | Austin | EP | 0428479 A1 | 5/1991 | |
| 6,955,658 B2 | 10/2005 | Murray, III | EP | 0423916 A1 | 4/1992 | |
| 7,004,966 B2 | 2/2006 | Edwin et al. | EP | 0483372 A1 | 5/1992 | |
| 7,021,114 B2 | 4/2006 | Perreault | EP | 0 517 075 A1 | 9/1992 | |
| 7,056,323 B2 | 6/2006 | Mareiro et al. | EP | 0 062 300 A2 | 10/1992 | |
| 7,060,218 B2 | 6/2006 | Skinner et al. | EP | 0517075 A1 | 12/1992 | |
| 7,112,298 B2 | 9/2006 | Kampa et al. | EP | 0 540 290 A2 | 5/1993 | |
| 2001/0001890 A1 | 5/2001 | Austin | EP | 0 541 443 A1 | 5/1993 | |
| 2002/0098373 A1 | 7/2002 | Wang et al. | EP | 0540290 A2 | 5/1993 | |
| 2002/0125617 A1 * | 9/2002 | Skinner et al. ................ 264/535 | EP | 0540290 B1 | 5/1993 | |
| 2003/0204238 A1 | 10/2003 | Tedeschi | EP | 0541443 A1 | 5/1993 | |
| 2003/0208254 A1 | 11/2003 | Shortt | EP | 0 303 889 B1 | 6/1993 | |
| 2004/0177805 A1 | 9/2004 | Hijlkema et al. | EP | 0 303 889 B1 | 9/1993 | |
| 2005/0240254 A1 | 10/2005 | Austin | EP | 0 606 165 A1 | 7/1994 | |
| 2006/0100694 A1 | 5/2006 | Globerman | EP | 0 562 478 B1 | 12/1994 | |
| | | | EP | 0 630 623 A2 | 12/1994 | |
| | FOREIGN PATENT DOCUMENTS | | EP | 0 688 545 A1 | 12/1995 | |
| AU | 61333/90 A | 2/1991 | EP | 0 697 226 A1 | 2/1996 | |
| AU | 61333/90 B | 2/1991 | EP | 0729767 B1 | 9/1996 | |
| AU | 53198/94 B | 3/1994 | EP | 0 800 801 A1 | 10/1997 | |
| CA | 2211694 | 2/1998 | EP | 0 826 346 A1 | 3/1998 | |
| CH | 513567 | 11/1971 | EP | 0 873 731 A1 | 10/1998 | |
| DE | 464004 | 7/1928 | EP | 0 916 318 | 5/1999 | |
| DE | 2001535 | 7/1970 | EP | 0 938 877 Aw | 9/1999 | |
| DE | 1665771 | 1/1971 | EP | 0 938 880 A3 | 11/1999 | |
| DE | 2301075 | 7/1973 | EP | 1295570 | 3/2003 | |
| DE | 2410933 | 9/1974 | FR | 975797 | 3/1951 | |
| DE | 118673 | 3/1976 | FR | 1571240 | 6/1969 | |
| DE | 2708945 | 9/1978 | FR | 2476524 | 8/1981 | |
| DE | 2920223 | 11/1980 | FR | 4-25755 | 2/1992 | |
| DE | 3205942 A1 | 9/1983 | FR | 2 677 872 A1 | 12/1992 | |
| DE | 3516862 A1 | 11/1986 | FR | 2677872 A1 | 12/1992 | |
| DE | 36 40 745 A1 | 6/1987 | GB | 159065 | 2/1921 | |
| DE | 3460745 C2 | 6/1987 | GB | 1205743 | 9/1970 | |
| DE | 3733749 A1 | 1/1988 | GB | 1583192 | 1/1981 | |
| DE | 38 23 060 A1 | 1/1989 | GB | 2 070 490 A | 9/1981 | |
| DE | 3823060 A1 | 1/1989 | GB | 1070490 A | 9/1981 | |
| DE | 3724479 A1 | 2/1989 | GB | 2 088 811 A | 6/1982 | |
| DE | 69029114 T2 | 11/1996 | GB | 2092894 A | 8/1982 | |
| DE | 195 37 872 A1 | 4/1997 | GB | 2 135 585 A | 9/1984 | |
| DE | 297 14857 U1 | 11/1997 | JP | 61125496 A | 15/1987 | |
| DE | 198 13 854 | 9/1999 | JP | 58-501458 | 9/1983 | |
| DK | 0417928 T3 | 12/1996 | JP | 60-50020 | 4/1985 | |
| EP | 0062300 A2 | 10/1982 | JP | 61-41444 | 2/1986 | |
| EP | 0 201 466 A2 | 4/1986 | JP | 62-213762 | 9/1987 | |
| EP | 0177330 A2 | 4/1986 | JP | 62-231657 | 10/1987 | |
| EP | 0177453 A2 | 4/1986 | JP | 62-235496 A | 10/1987 | |
| EP | 0183372 A1 | 6/1986 | JP | 63-214264 | 9/1988 | |
| EP | 0190543 A1 | 8/1986 | JP | 63-246178 | 10/1988 | |
| EP | 0 221 570 A2 | 5/1987 | JP | 63-28990 | 11/1988 | |
| EP | 0221570 A2 | 5/1987 | JP | 64-83685 | 3/1989 | |
| EP | 0256986 A2 | 2/1988 | JP | 64-83685 A | 3/1989 | |
| EP | 0274846 A1 | 7/1988 | JP | 01145076 A | 6/1989 | |
| EP | 0282175 A1 | 9/1988 | JP | 1-299550 | 12/1989 | |
| EP | 0 380 668 B1 | 10/1988 | JP | 2-174859 | 7/1990 | |
| EP | 0290138 A2 | 11/1988 | JP | 2174859 | 7/1990 | |

| | | |
|---|---|---|
| JP | 02180275 | 7/1990 |
| JP | 2-255157 | 10/1990 |
| JP | 02-255157 | 10/1990 |
| JP | 3-9745 | 1/1991 |
| JP | 3-9745 A | 1/1991 |
| JP | 3-9746 A | 1/1991 |
| JP | 39746 | 1/1991 |
| JP | 3-57465 | 3/1991 |
| JP | 3-151983 | 6/1991 |
| JP | 04-25755 | 2/1992 |
| JP | 4-25755 | 2/1992 |
| JP | 5-267998 | 10/1993 |
| JP | 747135 | 2/1995 |
| JP | 767967 | 3/1995 |
| JP | 1119230 | 1/1999 |
| LU | 79208 | 10/1979 |
| SU | 660689 | 5/1979 |
| SU | 764684 | 9/1980 |
| SU | 1084091 | 4/1984 |
| SU | 1217402 A | 3/1986 |
| SU | 145921 A1 | 2/1989 |
| WO | WO 83/03752 A1 | 11/1983 |
| WO | WO 84/00121 A1 | 1/1984 |
| WO | WO 89/01798 A1 | 3/1989 |
| WO | WO 89/08433 A1 | 9/1989 |
| WO | WO 91/07139 A1 | 5/1991 |
| WO | WO 91/17720 A1 | 11/1991 |
| WO | WO 92/06734 A1 | 4/1992 |
| WO | WO 92/09246 A1 | 6/1992 |
| WO | WO 93/06780 | 4/1993 |
| WO | WO 94/17754 A1 | 8/1994 |
| WO | WO 95/23563 A1 | 9/1995 |
| WO | WO 95/26695 A2 | 10/1995 |
| WO | WO 96/09013 A1 | 3/1996 |
| WO | WO 96/26689 A1 | 9/1996 |
| WO | WO 97/09946 | 3/1997 |
| WO | WO 98/14120 | 4/1998 |
| WO | WO 98/19633 | 5/1998 |
| WO | WO 98/22159 A2 | 5/1998 |
| WO | WO 98/48734 A1 | 11/1998 |
| WO | WO 99/02105 A1 | 1/1999 |
| WO | WO 99/43473 | 9/1999 |
| WO | WO 99/55406 | 11/1999 |
| WO | WO 01/21103 | 3/2001 |
| WO | 02066095 A2 | 8/2002 |
| WO | 02102283 A1 | 12/2002 |
| WO | 2005053937 | 6/2005 |
| WO | 2006110861 | 10/2006 |

OTHER PUBLICATIONS

Alvarado, R., et al., "Evaluation of Polymer-Coated Balloon-Expandable Stents in Bile Ducts," *Radiology*, 170, 3: 975-978, Mar. 1989.

American Heart Association 61st Scientific Sessions. Abstract Form. "A New Percutaneous Expandable Stent.".

Baier, R., et al., "Initial Events in Interaction of Blood with a Foreign Surface," *Journal of Biomedical Material Research*, 3: 191-206, 1969.

Balko, A., et al., "Transfemoral Placement of Intraluminil Polyurethane Prosthesis for Abdominal Aortic Aneurysm," *Journal of Surgical Research*, 40: 305-309, 1986.

Becker, G., et al., "Early Experience with the Palmaz Stent in Human Iliac Angioplasty," *Indiana Medicine*, 286-292, Apr. 1989.

Becker, G., et al., "Simultaneous Angioplasty and Intraluminal Grafting with the Palmaz Expandable Intraluminal Graft," 72nd *Scientific Assembly and Annual Meeting of the Radiological Society of North America*, Chicago, Nov./Dec. 1986.

Bonzel, T., et al., "The Sliding Rail System (Monorail): Description of a New Technique for Intravascular Instrumentation and its Application to Coronary Angioplasty," *Kardologie*, Supplement 6: 119-122, 1987.

*Brochure*: "Anomatic II Positioning Controller," printed by Anorad Corporation.

C.R. Bard, PE Plus Peripheral Balloon Dilatation Catheter, *C.R. Bard Inc.*, Aug. 1985.

Campbell, C., et al., "Expanded Microporous Polytetrafluoroethylene as a Vascular Substitute: A Two Year Follow-up," *Surgery*, 85, No. 2: 177-183, Feb. 1979.

Carrasco, C., et al., "Expandable Biliary Endoprosthesis: An Experimental Study," *American Journal of Roentgenology*, 145: 1279-1281, Dec. 1985.

Castaneda-Zuniga, W., ed., Tranluminal Angioplasty, 1983.

Charnsangavej, C., M.D., et al., Endovascular Stent for Use in Aortic Dissention: An In Vitro Experiment, *Radiology*, pp. 323-324, vol. 157, No. 2, Nov. 1985.

Charnsangavej, C., M.D., et al., A New Expandable Metallic Stent for Dilation of Stenotic Tubular Structures Experimental and Clinical Evaluation, *Houston Medical Journal*, 3, No. 2: 41-51, 1987.

Charnsangavej, C., M.D., et al., Stenosis of the Vena Cava: Preliminary Assessment of Treatment With Expandable Metallic Stents, *Radiology*, pp. 295-298, vol. 161, Nov. 1986.

Cimochowski, G., et al., "Greenfield Filter Versus Mobin-Uddin Umbrella," *Journal of Thoracic and Cardiovascular Surgery*, 79, No. 3: 358-365, Mar. 1980.

Coons, H., et al, "Large-Bore, Long Biliary Endoprostheses (Biliary Stents) for Improved Drainage," *Radiology*, 148, No. 1: 89-94, Jul. 1983.

Cope, C., "Balloon Dilatation of Closed Mesocaval Shunt;," *American Journal of Roentgenology*, 135: 989-993, Nov. 1980.

Cragg, A., et al., "A New Percutaneous Vena Cava Filter," *American Journal of Roentgenology*, 141: 601-604, Sep. 1983.

Cragg, et al., Non-Surgical Placement of Arterial Endoprostheses: A New Technique Using Nitinol Wire, *Radiology Journal*, pp. 261-163, Apr. 1983.

Cragg, A., et al., "Percutaneous Arterial Grafting," *Radiology*, 150, No. 1: 45-49, Jan. 1984.

Culverwell, M., "Angioplasty Stents May Prevent Restenosis," *Carcio*, 11-13, Jan. 1987.

Dalessandri, K., et al., "The Effect of Lumbar Sympathectomy on Postsynaptic Vascular Smooth Muscle Response in the Lower Limb in Dogs," *Cardiovascular and Interventional Radiology*, 11: 82-85, 1988.

De Palma, V., et al., "Investigation of Three Surface Properties of Several Metals and their relation to Blood Compatibility," *Journal of Biomedical Materials Research Symposium*, 3: 37-75, 1972.

Denny, D., et al., "Percutaneous Kimray-Greenfield Filter Placement by Femoral Vein Puncture," *American Journal of Roentgenology*, 145: 827-829, Oct. 1985.

Deriu, G., et al., "The Rationale for Patch-Graft Angioplasty After Carotid Endarterectomy: Early and Long-Term Follow-Up," *Stroke*, 15: No. 6: 972-979, Nov. 1984.

Dichek, D.A., et al., "Seeding of Intravascular Stents with Genetically Engineered Endothelial Cells," *Circulation*, 80: 1237-1353, 1989.

Dorros, G., et al., "Clinical Research: Angioplasty," *Circulation* (Supplement), 74, No. 1448: II-363, 1986.

Dotter, C., "Interventional Radiology—Review of an Emerging Field," *Seminars in Roentgenology*, 16, No. 1, Jan. 1981.

Dotter, Charles T. Transluminal Expandable Nitinol Coil Stent Grafting: Preliminary Report, *Radiology Journal*, pp. 259-260, Apr. 1983.

Dotter, C., et al., "Transluminal Treatment of Arteriosclerotic Obstruction," *Circulation*, 30: 654-670, Nov. 1964.

Dotter, Charles T., Transluminally Placed Coilspring Endarterial Tube Grafts, *Investigative Radiology*, pp. 329-332, Sep./Oct. 1969.

Duprat, G., et al, "Self-expanding Metallic Stents for Small Vessels: An Experimental Evaluation," *Radiology*, 192: 469-472, 1987.

Duprat, G., et al., "Flexible Balloon-Expanded Stent for Smail Vessels, Work in Progress," *Radiology*, 162: 276-278, 1987.

Edwards, W., "Arterial Grafts," *Archives of Surgery*, 113, No. 9: 1225-1233, Nov. 1978.

Eichelter, P., et al., Prophylaxis of Pulmonary Embolism, *Archives of Surgery*, 97: 348-356, Aug. 1968.

Fallone, B., "Elastic Characteristics of the Self-Expanding Metallic Stents," *Investigative Radiology*, 23: 370-376, 1988.

Finci, L., et al, "Percutaneous Transluminal Coronary Angioplasty of Bifurcation Narrowing Using the Kissing Wire Monorail Balloon Technique," *The American Journal of Cardiology*, Apr. 1987.

Fogarty, T., et al., "Adjunctive Intraoperative Arterial Dilation: Simplified Instrumentation Technique," *Archives of Surgery*, 116: 1391-1398, 1981.

Fogarty, T., et al., "Current Status of Dilatation Catheters and Guiding Systems," *American Journal of Cardiology*, 53, No. 12: 97C-100C, Jun. 1984.

Fogarty, T., et al., "Intraoperative Coronary Artery Balloon-Catheter Dilation," *American Heart Journal*, 107, No. 4: 845-851, 1984.

Frimberger, E., "Expanding Spiral—A New Type of Prosthesis for the Palliative Treatment of Malignant Esophageal Stenoses," *Endoscopy*, 15: 213-214, 1983.

Furui, S., M.D., et al., Hepatic Inferior Vena Cava Obstruction: Treatment of Two Types with Gianturco Expandable Metallic Stents, *Radiology*, pp. 665-670, vol. 176, No. 3, Sep. 1990.

Gardner, R., et al., "The Surgical Experience and a One to Sixteen Year Follow-Up of 277 Abdominal Aortic Aneurysms," *American Journal of Surgery*, 135, No. 1: 226-230, Jan. 1978.

Goldstein, H., et al, "Transcatheter Occlusion of Abdominal Tumors," *Radiology*, 120, No. 3: 539-545, Sep. 1976.

Greenfield, L., et al, "A New Intracaval Filter Permitting Continued Flow and Resolution of Emboli," *Surgery*, 73, No. 4: 599-606, Apr. 1973.

Gunther, R., et al, "Percutaneous Nephropyelsotomy Using a Fine-Needle Puncture Set," *Radiology*, 132, No. 1: 228-230, Jul. 1979.

Gunther, R., et al., "Vena Caval Filter to Prevent Pulmonary Embolism: Experimental Study," *Radiology*, 156, No. 2: 315-320, Aug. 1985.

Harries-Jones, E., et al., "Repositioning of Biliary Endoprosthesis with Gruntzig Balloon Catheters," American Journal of Roentgenology, 138: 771-772, Apr. 1982.

Harrington, J., et al., "The Palmaz-Schatz Stent," *Handbook of Cardiovascular Interventions/Vascular Interventions*, 536-572.

Hoevels, J., et al., "Percutaneous Transhepatic Insertion of a Permanent Endoprosthesis on Obstructive Lesions of the Extrahepatic Bile Ducts," *Gastrointestinal Radiology* 4: 367-377, 1979.

Honickman, S., et al., "Malpositioned Biliary Endoprosthesis," *Radiology*, 144: 423-425, Jul. 1982.

Hunter, J., et al., "Experimental Balloon Obstruction of the Inferior Vena Cava," *Annals of Surgery*, 171, No. 2: 315-320, Feb. 1970.

IBM Technical Disclosure Bulletin; Band 11, No. 9, Feb. 1969, Seite 1151, New York, US J.F. Smith u.a.: "Selectively removing dielectric materials".

Inoue, K., et al., "Clinical Application of Transvenous Mitral Commissurotomy by a New Balloon Catheter," *Thoracic Cardiovascular Surgery*, 87, No. 3: 394-402, Mar. 1984.

*Journal of the American College of Cardiology* (Supplement A): 106A, (from Abstracts of the 36th Annual Scientific Session, American College of Cardiology, New Orleans, Louisiana, Mar. 8-12, 1987), Elsevier (Feb. 1987).

Kaltenbach, M., Abstracts, *Zeitschrift fur Kardiologie*, Apr. 3, 1991 (German only).

Kan, J., et al., "Percutaneous Balloon Valvuloplasty: A New Method for Treating Congenital Pulmonary-Valve Stenosis," *New England Journal of Medicine*, 307, No. 9, 540-542, 1982.

Kerlan, R., et al., "A Simple Method for Insertion of Large Untapered Catheters," *American Journal of Roentgenology*, 141: 792, 1983.

Kerlan, R., et al., "Biliary Endoprostheses: Insertion Using a Combined Peroral-Transhepatic Method," *Radiology*, 150, No. 3: 828-830, 1984.

Lababidi, Z., et al., "Percutaneous Balloon Aortic Valvuloplasty: Results in 23 Patients," *American Journal of Cardiology*, 53: 194-197, Jan. 1984.

Lary, B., et al., "The Experimental Use of Steel Mesh Tubes for Replacement Arterial Segments," *AMA Archives of Surgery*, 72: 69-75, Jan. 1956.

Lawrence, D., et al., "Percanteous Endovascular Graft: Experimental Evaluation," *Radiology*, 163: 357-360, 1987.

Lewandowski, B., et al., "The Air-Filled Hepatic Duct: The Saber Sign as an Aid to the Radiographic Diagnosis Pneumobilia," *Radiology*, 153, No. 2: 329-332, Nov. 1984.

Lund, G., et al., "A New Vena Caval Filter for Percutaneous Placement and Retrieval: Experimental Study," *Radiology*, 152, No. 2: 369-372, Aug. 1984.

Lunderquitst, A., et al.,"Guidewire for Percutaneous Transhepatic Cholangiography," *Radiology*, 132, No. 1: 228, Jul. 1979.

Maass, et al., Radiological Follow-Up of Transluminally Inserted Vascular Endoprostheses: An Experimental Study Using Expanding Spirals, *Radiology Journal*, pp. 659-663, 1984.

Meenaghan, M., et al., "Tissue Response to Surface-Treated Tantalum Implants: Preliminary Observations in Primates," *Biomedical Materials Research*, 13, No. 4: 631-543, Jul. 1979.

Mirich, D., et al., "Percantaneously Placed Endovascular Grafts for Aortic Aneurysms: Feasibility Study," *Radiology*, 170: 1033-1037, 1989.

Mobin_Uddin, K., et al., "The Inferior vena Cava Umbrella Filter," *Progress in Cardiovascular Diseases*, 17, No. 5: 391-399, Mar./Apr. 1975.

Mobin-Uddin, K., et al., "Caval Interruption for Prevention of Pulmonary Embolism," *Archives of Surgery*, 99: 711-715, Dec. 1969.

Muller, D., et al., "Advances in Coronary Angioplasty: Endovascular Stents," *Coronary Artery Disease*, I: 438, Jul./Aug. 1990.

Mullins, C., et al., "Implantation of Balloon-Expandable Intravascular Grafts by Cathertization in Pulmonary Arteries and Systemic Veins," *Circulation*, 77: 188-189, 1918.

Nanda, R., et al., "Effect of Maxillary Osteotomy on Subsequent Craniofacial Growth in Adolescent Monkeys," *American Journal of Orthod.*, 83: 391-407, May 1983.

Palestrant, Al., et al., " Comparative In Vitro Evaluation of the Nitinol Inferior Vena Cava Filter," *Radiology*, 145: 351-355, Nov. 1982.

Palmaz, J., "Balloon Expandable Intra-Arterial Stents: Effect of Anticoagulation on Thrombus Formation," *Circulation* (Supplement Part II), 76, No. 4: 180, Oct. 1987.

Palmaz, J., "Balloon-Expandable Intravascular Stent," *American Journal of Roentgenology*, 150: 1263-1269, Jun. 1988.

Palmaz, J., "Chapter 30: Overview of Intravascular Stents", in Kim, D., et al., *Peripheral Vascular Imaging and Intervention*, 507-508, 1992.

Palmaz, J., "Die intraluminale Sten-Implantation Nach Palmaz," *Radiologe*, 11: 560-563, 1987.

Palmaz, J "Expandable Intraluminal Vascular Graft: A Feasibility Study," *Surgery*, 2: 199-205, 1986.

Palmaz, J., et al., "Atherosclerotic Rabbit Aortas: Expandable Intraluminal Grafting," *Radiology*, 3: 723-726, 1986.

Palmaz, et al., Expandable Intraluminal Graft: A Preliminary Study, *Radiology Journal*, pp. 73-77, 1985.

Palmaz, J., et al., "Balloon Expandable Intraluminal Grafting of Normal and Abnormal Renal Arteries: Experimental Study," 72nd Scientific Assembly and Annual Meeting, Radiology Society of North America, Chicago, 1-23 [plus figures], Nov. 1986.

Palmaz, J., et al., "Balloon-Expandable Intraarterial Stents: Effect of Antithrombotic Medication on Thrombus Foramtion," *Pros and COns in PTA and Auxiliary Methods*, 170-178, 1989.

Palmaz, J., et al., Early Endothelisation of Balloon-expandable Stents: Experimental Observations, *Journal of Interventional Radiology*, 3: 119-124, 1988.

Palmaz, J., et al., "Expandable Intrahepatic Portacaval Shunt Stents: Early Experience in the Dog," *American Journal of Roentgenology*, 145: 821-825, 1985.

Palmaz, J., et al., "Expandable Intrahepatic Portacaval Shunt Stents in Dogs with Chronic Portal Hypertension," *American Journal of Roentgenology*, 147: 1251-1254, 1986.

Palmaz, J., et al., "Intraluminal Stents in Arterosclerotic Iliac Artery Stenosis: Preliminary Report of Multicenter Study, "*Radiology*, 168, No. 3: 727-731, Sep. 1988.

Palmaz, J., et al., "Normal Stenotic Renal Arteries: Experimental Balloon-Expandable Intraluminal Stenting," *Radiology*, 164: 705-708, Sep. 1987.

Palmaz, J., et al., "Removable Biliary Endoprosthesis," *American Journal of Roentgenology*, 140: 812-814, Apr. 1983.

Palmaz, J., Monograph (1980).

Palmaz, J., Monograph (May 18, 1983).

Palmaz, J., *The Current Status of Vascular Prosthesis*, Presentation of The Society of CV & Interventional Radiology Twelfth Annual Course on *Diagnostic Angiography and Interventional Radiology*, 118-120, Mar. 23-26, 1987.

Papanicolaou, N., et al., "Insertion of a Biliary Endoprosthesis Using a Balloon Dilation Catheter," *Gastrointestinal Radiology*, 10: 394-396, 1985.
Pate, J. et al., "A New Form of Vena Caval Interruption, "*Annals of Surgery*, 169, No. 6, 873-880, Jun. 1969.
Program: Day 2 (Nov. 18) The Radiological Society of North America, Radiology, Chicago: Nov. 30-Dec. 5, 1986, Special Edition, vol. 161(P).
Puel, J., et al., "Intravascular Stents to Prevent Restenosis After Transluminal Coronary Angioplasty," *Circulation* (Supplement Part II), 76, No. 4: 0105, Oct. 1987.
Rashkind, W., et al., "Creation of an Atrial Septal Defect Without Thoracotomy: A Palliative Approach to Complete Transposition of the Great Arteries," *Journal of the American Medical Association*, 196: 173-174, Jun. 1966.
Rees, C., et al., "Angioplasty and Stenting of Completely Occuluded Iliac Arteries," *Radiology* (Part 2), 172, No. 3, 953-959, Sep. 1989.
Rees, C., et al., "DSA in Acute Gastrointestinal Hemorrhage: Clinical and in Vitro Studies," *Radiology*, 169, No. 2: 499-503, Nov. 1988.
Rees, C., et al., "The Hemodynamic Effects of the Administration of Ionic and Nonionic Contrast Materials into the Pulmonary Arteries of a Canine Model of Acute Pulmonary Hypertension," *Investigative Radiology*, 23, No. 3: 184-189, Mar. 1988.
Richter, G., et al., "Der Transjuguslacre Intrahepatische Portosystemische Stent-Shunt (TIPSS); Eine Neue Nichtoperative, Perkutane Methode," *Radiologe*, 29: 406-411 , 1989.
Richter, G., et al., "Die Behandlung eines akuten Becker arterienverschlusses durch Katheterlyse, Katheterdilatation and Implantation einer neuartigen metallischen Gefa.beta.ednoprothese," *Der chirurg*, 60, No. 5: 346-351, May 1989.
Ring, E., et al., "A Simple, Indwelling Biliary Endoprosthesis Made From Common Available Catheter Material," *American Journal of Roentgenology*, 139: 615-617, Sep. 1982.
Roehm, J., et al., "Percutaneous Transcatheter Filter for the Interior Vena Cava," *Radiology*, 150, No. 1: 255-257, Jan. 1984.
Roland, M., Spiral Teflon Stent for Tuboplasty Involving Fimbria, *Obstetrics Gynecology*, 36: 359-362. 1970.
Rollins, N., et al., "Self-expanding Metallic Stents: Preliminary Evaluation in an Atuaroschlerotic Model," *Radiology*, 163, No. 3: 739-742, Jun. 1987.
Rosch, J., et al., "Gianturco Expandable Wire Stents in the Treatment of Superior Vena Cava Syndrome Recurring After Maximum-Tolerance Radiation," *Cancer*, 60: 1243-1246, 1987.
Rösch, J., M.D., et al., Experimental Intrahepatic Portacaval anastomosis: Use of Expandable Gianturco Stents, *Radiology*, pp. 481-485, vol. 162, Feb. 1987.
Rösch, J., M.D., et al., *Gianturco Expandable Stents in Experimental and Clinical Use*, paper presented at the Twelfth Annual Course on "Diagnostic angiography and Interventional Radiology" Mar. 23-26, 1987 (Pittsburgh, Pennsylvania).
Rösch, J., M.D., et al., TransjugularIntrahepatic Portacaval Shunt: An Experimental Work, *The American Journal of Surgery*, pp. 588-592, vol. 121, May 1971.
Rosch, J., et al., "Modified Gianturco Expandable Wire Stents in Experimental and Clinical Use," *Annales de Radiologie*, 31, No. 2: 100-103, 1987.
Portacaval Shunt: An Experimental Work, *American Journal of Surgery*, 121: 588-592, May 1971.
Roubin, G., et al., "Early and Late Results of Intracoronary Arterial Stenting After Coronary Angioplasty in Dogs," *Circulation*, 4: 891-897, 1987.
Rousseau, H., et al., "Percutaneous Vascular Stent: Experimental Studies and Preliminary Clinical Results in peripheral Arterial Diseases," *Inter. Angio.*, 6: 153-161, 1987.
Rousseau, H., et al., "Self-Expanding Endovascular Prosthesis: An Experimental Study," *Radiology*, 164: 709-714, Sep. 1987.
70th Scientific Assembly and Annual Meeting: Scientific Program, *Radiology*, Washington, D.C., Nov. 25-30, 1984, Special Edition, vol. 153(P).
72nd Scientific Assembly and Annual Meeting: RSNA Scientific Program, *Radiology*, Chicago: Nov. 30-Dec. 5, 1986, Special Edition, vol. 161(P).

Saunders, W., "Dorland's Illustrated Medical Dictionary, " 675 & 759, 26th Edition, 1981.
Schatz, R., "Introduction to Intravascular Stents," *Cardiology Clinics*, 6, No. 3: 357-372, 1988.
Schatz, R., et al., "A View of Vascular Stents," *Circulation*, 79: 445-457, 1989.
Schatz, R., et al., "Balloon Expandable Intracoronary Stunts in Dogs," *Circulation* (Supplement Part II), 74; II-458, 1824, 1986, 1986.
Schatz, R., et al., "Balloon Expandable Intravascular on Grafts," 16th *Annual Symposium of the Texas Health Institute—International Symposium on Interventional Cardiology*, Houston, Sep. 1986.
Schatz, R., et al., "Balloon-Expandable Intracoronary Stents in the Adult Dog," *Circulation*, 76, No. 2 450-457, 1987.
Schatz, R., et al., "Intravascular Stents for Angioplasty," *Cardio*, 27-31, Dec. 1987.
Schatz, R., et al., "New Technology in Angioplasty: Balloon-Expandable Intravascular Stents," *New Developments in Medicine*, 2, No. 2: 59-75, Sep. 1987.
Sechler, E.S., *Elasticity in Engineering*, 1956.
Semb, B., et al., "Balloon Valvulotomy of Congenital Pulmonary Valve Stenosis with Tricuspid Valve Insufficiency," *Cardiovascular Radiology*, 2: 239-241, 1979.
Sigwart, U., et al., "Initial Experience With a New Approach to Stenting of Peripheral and Coronary Arteries.".
Sigwart, U., et al., "Intravascular Stents to Prevent Occlusion and Restenosis After Transluminal Angioplasty," *New England Journal of Medicine*, 316: 701-706, 1987.
Sigwart, U., et al., "One Year of Percutaneous Coronary Stenting," *Circulation* (Supplement Part II), 76, No. 4: 0104, Oct. 1987.
Simon, M., et al., "A Vena Cava Filter Using Thermal Shape Memory Alloy," *Radiology*, 125: 89-94, Oct. 1977.
Simonds, A.K., et al., "Use of Expandable Metal Stents in the Treatment of Bronchial Obstruction," *Thorax*, 44: 680, May 1989.
Smith, D., et al., "Safe and Effective Catheter Angiography Through Prosthetic Vascular Grafts," *Radiology*, 138, No. 2: 487-488, Feb. 1981.
Solberg, S., et al, "Cold Induced Endothelial Cell Detachment in Human Sephenous Vein Grafts," *Journal of Cardiovascular*, 28, No. 5: 571-575, Sep.-Oct. 1987.
Soviet Inventions Illustrated, week 84, Jan. 16, 1985, No . 48, M21 P51, Derwent Publications Ltd., London, GB.
Stack, R., et al., "A New Highly Flexible Balloon-Expandable Endovascular Stent: Initial Experimental Results and Up to Six Months Follow-up," *Laser One Meeting*, Newport Beach, California, May 11-13, 1989.
Strecker, E., et al., "A New Vascular Balloon-expandable Prosthesis—Experimental Studies and First Clinical Results," *Journal of Interventional Radiology*, 3: 59-62, 1988.
Strecker, E., et al., "Perkutan Implantierbare, Durth Balloon Aufdehnbare Gefa.beta.prothese," *Dtsch Med Wschr*, 113, No. 4, 538-542, 1988.
Strupp, G., et al., "Clinical and Angiographic Short and Medium Term Results After Coronary Stenting," *Z kardiol*, 81: 500, 1992 (German with English language summary).
Teplick, S., et al., "A New Biliary Endoprosthesis," *American Journal of Roentgenology*, 141: 799-801, Oct. 1983.
Timoshenko, S.P., *Strength of Materials*, Part I, Elementary Theory and Problems, 1930.
Timoshenko, S.P., et al., *Theory of Elastic Stability*, 1961.
Topol, E., *Textbook of Interventional Cardiology*, Chapter 30, by S. Ellis, 623-632, 1990.
Toshiyuki, I., et al., "Relocatable Gianturco Expandable Metallic Stents," *Radiology*, 178: 575, Feb. 1991.
Trent, M., et al., "A Balloon-Expandable Intravascular Stent for Obliterating Experimental Aortic Dissection," *Journal of Vascular Surgery*, 11: 707-717, May 1990.
Uchida, B., et al., "Modifications of Gianturco Expandable Wire Stents," *American Journal of Roentgenology*, 150: 1185-1187, 1988.
Van Der Giessen, W., et al., "Coronary Stenting With a New, Radiopaque, Balloon-Expandable Endoprosthesis in Pigs," *Circulation*, 83: 1788-1798, 1991.

Wallace, Michael J., et al., Tracheobronchial Tree: Expandable Metallic Stents Used in Experimental and Clinical Applications (Work in Progress), *Radiology* pp. 309-312, vol. 158, Feb. 1986.

Yoshimura, H., et al., "Afterloading Intracavitary Irradiation and Expanding stent for Malignant Biliary Obstruction," Radiation Medicine, 7: 36-41, 1989.

Yoshioka, T., et al., "Development and Clinical Application of Biliary Endoprosthesis Using Expandable Metallic Stents," *Japan Radiological Society*, 48: 1183-1185, 1988.

Yoshioka, T., et al., "Expandable Metallic Biliary Endoprostheses: Preliminary Clinical Evaluation," *Radiology*, 117: 253-257, 1990.

Yoshioka, T., et al., "Self-Expanding Endovascular Graft: An Experimental Study in Dogs," *AJR*, 151: 673-676, 1988.

Rösch, J., M.D., et al., TransjugularIntrahepatic Portacava! Shunt: An Experimental Work, *The American Journal of Surgery*, pp. 588-592, vol. 121, May 1971.

C.R. Bard, PE Plus Peripheral Balloon Dilatation Catheter, *C.R. Bard*, Inc. Aug. 1985.

Wright, et al., Percutaneous Endovascular Stents: An Experimental Evaluation, *Radiology Journal*, pp. 69-72, 1985.

Charnsangavej, C., M.D., et al., Endovascular Stent for Us: in Aortic Dissention: An in Vitro Experiment, *Radiology*, pp. 323-324, vol. 157, No. 2, Nov. 1985.

Wallace, Michael J., et al., Tracheobronchial Tree: Expandable Metallic Stents Used in Experimental and Clinical Applications (Work in Progress), *Radiology*, pp. 309-312, vol. 158, Feb. 1986.

Duprat, et al., Flexible Balloon-Expanded Stem for Small Vessels, *Radiology Journal*, pp. 276-178, 1987.

US 2006/100694, Filing Date: Nov. 5, 2006.

User Manual *TOMINATOR™ Stent Crimping Equipment* (Undated).

Bard XT Stent Brochure: *The cXTraordinary Sent* (Undated).

*Corporate Profile—Machine Solutions, Inc.*, Reprinted from *European Medical Device Manufacturer*, Jul./Aug. 2000, Copyright © 2000 Canon Communications LLC.

MSI Equipment pages, www.machinesolutions.org Copyright © 2002 Machine Solutions, Inc.

\* cited by examiner

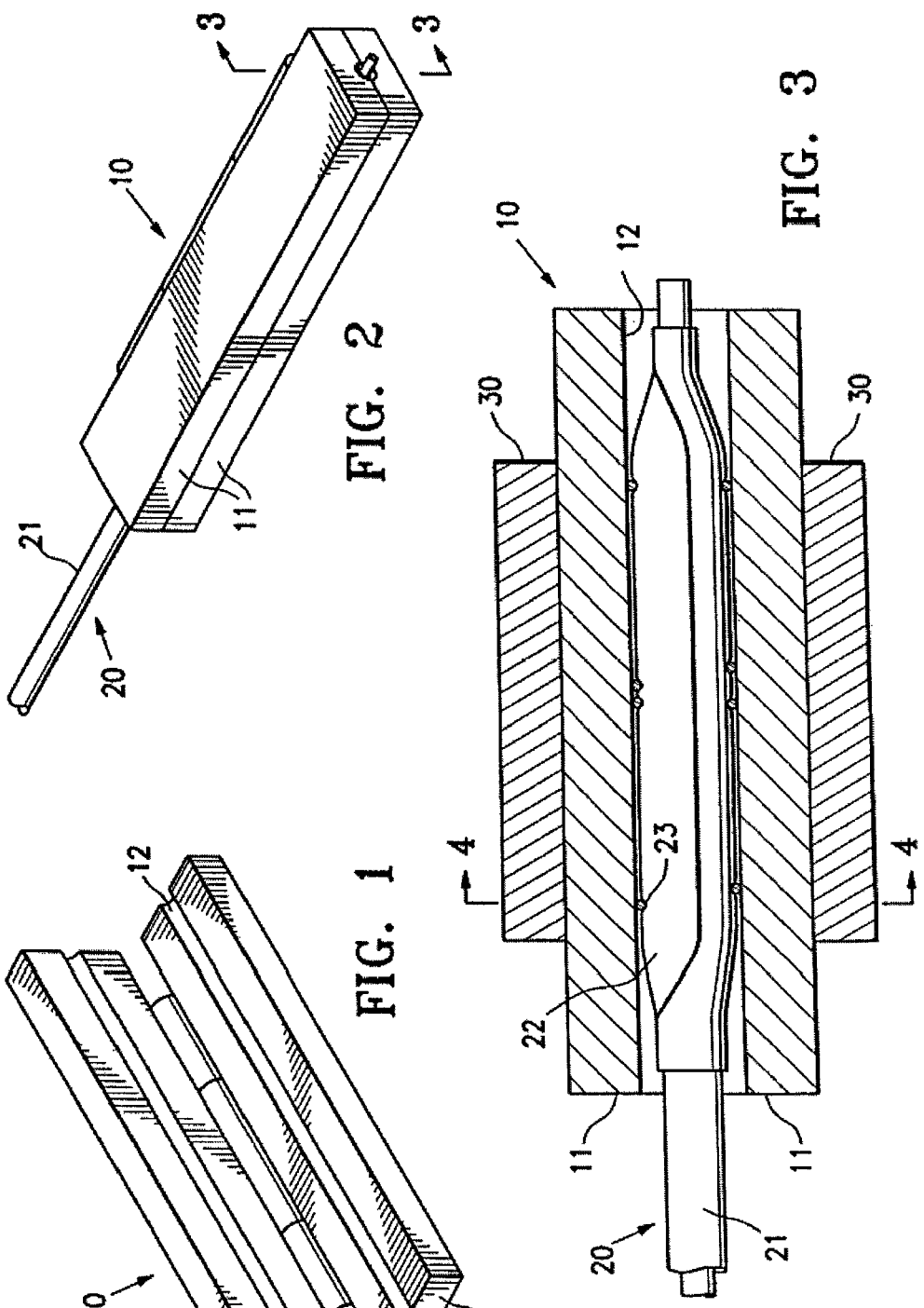

METHOD FOR RETAINING A VASCULAR STENT ON A CATHETER

CROSS-REFERENCES TO RELATED APPLICATIONS

This application is a division of U.S. Ser. No. 11/521,993 filed Sep. 15, 2006 and is now U.S. Pat. No. 7,947,207, which is a continuation-in-part of U.S. Ser. No. 11/453,747 filed Jun. 15, 2006 and is now U.S. Pat. No. 7,763,198, which is a continuation-in-part of U.S. Ser. No. 11/105,085 filed Apr. 12, 2005 and is now U.S. Pat. No. 7,563,400, the entirety of which are incorporated herein by reference.

BACKGROUND OF THE INVENTION

This invention relates generally to catheters and stents, and particularly to methods for retention of stents on intravascular stent delivery catheters.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

The stent must be securely yet releasably mounted on the catheter balloon for delivery and deployment at the desired location in a patient's body lumen. If the stent becomes dislodged from or moved relative to the balloon during delivery, the system will not correctly implant the stent in the body lumen. However, the stent can't be so strongly fixed to the balloon that it inhibits expansion of the balloon and/or release of the stent once the balloon is positioned at the desired location. One difficulty has been retention of stents, including stents having a drug delivery layer. The mounting process used to secure the drug delivery stent to the balloon must not damage the stent. Furthermore, the stent retention process must not damage a stent including a drug or the matrix material containing the drug. It would be a significant advance to provide a catheter balloon having improved retention of a stent, for example, a drug delivery stent, and without inhibiting balloon or stent function. The present invention satisfies these and other needs.

SUMMARY OF THE INVENTION

One aspect of the present invention is a method of mounting a stent on a balloon catheter, including positioning the stent on a balloon of the balloon catheter, and applying a radially compressive force on an outer surface of the stent, thereby decreasing the outer diameter of the stent on the balloon catheter. The balloon is then pressurized and heated while restricting radial expansion of the outer surface of the stent during a first period of time. Thereafter, the balloon is then pressurized and heated while restricting radial expansion of the outer surface of the stent during a second period of time. In one aspect of the invention, the second time period may have a duration of about 15 seconds to about 48 hours. The balloon may be pressurized to a pressure of about 5 pounds per square inch (3.5 newtons per square centimeter) to about 300 pound per square inch (207 newtons per square centimeter) during at least one of the first time period and the second time period.

In one aspect, the pressurizing and heating of the balloon may be performed in a mold configured to restrict the radial expansion of the outer surface of the stent. In another aspect, the pressurizing and heating of the balloon may be performed in a sheath configured to restrict the radial expansion of the outer surface of the stent. Still another aspect of the present invention is restricting radial expansion of the outer surface of the stent to about a final stent outer diameter. Another aspect of the present invention is applying a transient plasticizing agent to the balloon prior to heating and pressurizing the balloon.

The heating of the balloon may be performed by applying heat using convection through the mold. The heating of the balloon may be performed by heating the mold by contacting a surface of the mold with a conductive heating element member which heats the mold purely by conduction and which provides temperature control to the mold with a tolerance of about ±1 degree to about ±2 degrees F. In one aspect, the heating of the balloon is performed by applying heat using forced air convection. In another aspect of the invention, the heating of the balloon is performed by applying heat using an oven. In still another aspect of the present invention, the balloon is heated to a temperature approximately equal to the glass transition temperature of the balloon during at least one of the first time period and the second time period.

In still another aspect of the invention the stent is a drug delivery stent and mounting the stent on the balloon and increasing stent retention is performed without damaging the drug delivery layer of the stent.

Yet another aspect of the present invention includes cooling the stent after applying heat and pressure to the balloon. The cooling may applied during a third period of time. The cooling may be controlled. In one aspect of the present invention, the balloon remains pressurized during the cooling.

Yet another aspect of the present invention is a method of mounting a stent on a balloon catheter, including positioning a stent on a balloon catheter, the balloon catheter having an elongated shaft with an inflation lumen and a guidewire lumen and an inflatable balloon on a distal shaft section with an interior in fluid communication with the inflation lumen, and the stent having an open-walled body of stent struts with gaps between adjacent stent struts. At least one radially compressive force is applied on an outer surface of the stent, thereby decreasing the outer diameter of the stent on the balloon catheter. Thereafter, the balloon is heated and inflation media is introduced into the interior of the balloon for a first period of time to radially expand the balloon with the stent restrained from radially expanding, wherein the balloon expands into the stent gaps to embed the stent in an outer surface of the balloon. The inflation media may then be removed from the balloon interior. Thereafter, the balloon is heated and inflation media is introduced into the interior of the balloon for a second period of time to radially expand the balloon with the stent restrained from radially expanding. The stent may be restrained from radially expanding by using a mold, for example a split mold, or a sheath. The balloon may further expand into the stent gaps to more securely embed the stent in an outer surface of the balloon. This may increase stent retention on the balloon catheter after sterilizing the stent, for example, by EtO sterilization.

One other aspect of the present invention is a method of increasing retention of an intravascular device on a balloon catheter, including crimping the intravascular device onto a balloon of the balloon catheter, a first stage of heating and pressurizing the balloon, and a second stage of heating and pressurizing the balloon. The method may further include crimping the intravascular device onto a balloon of the balloon catheter at least one additional time.

One aspect of the present invention is directed to a method of mounting a stent on a stent delivery balloon catheter. Yet another aspect of the invention is a method of mounting a drug delivery stent on a balloon, and a stent delivery balloon catheter produced therefrom. Still another aspect of the invention is a method that securely mounts a drug delivery stent on a balloon catheter without damaging the drug delivery layer of the stent.

In one aspect of the invention, the method generally comprises positioning a stent, for example, a drug delivery stent, on a balloon of a balloon catheter, and positioning the balloon with the stent thereon within a polished bore of a mold formed at least in part of a metallic material. In yet a further aspect of the invention, the stent is a drug delivery stent, and the balloon is pressurized and heated within the mold to mount the stent on the balloon, without damaging the drug delivery layer of the stent. The mold radially restrains the stent from expanding when the balloon is pressurized therein, so that the balloon can be forced into the gaps in the stent wall using inflation pressures higher than those which normally cause radial expansion of the stent. The bore of the mold is defined by a polished inner surface with a polished finish which is sufficiently smooth so that contact and relative movement between the stent and polished inner surface of the mold does not roughen or otherwise damage or create a texture on the drug delivery layer of the stent. As a result, the release rate of the drug from the drug delivery layer is substantially equal to the release rate prior to stent mounting. In another aspect of the invention, the smooth surface of the drug delivery layer, which is free of roughness and irregularities caused by the stent mounting, provides the drug delivery layer with a uniform thickness which is within the normal variance produced by the method used to form the drug delivery layer. Additionally, the inner surface of the mold does not cause the drug delivery layer to transfer drug to the inner surface of the mold during the stent mounting, so that the amount of drug present in the drug delivery layer is substantially equal to the amount prior to stent mounting.

In yet another aspect of the invention, the drug delivery layer of the stent is a coating applied to a surface of the radially expandable tubular body of the stent. However, a variety of suitable configurations may be used as are well known in the art, including embodiments in which the tubular body of the stent is itself formed of a drug delivery matrix, or the drug delivery layer is a tubular sleeve on a surface of the body of the stent. Additionally, the drug delivery layer should be understood to broadly refer to configurations which deliver or present one or more drugs by any of a variety of suitable mechanisms including eluting the drug from the layer, bioabsorption of a drug delivery matrix, and the like. The stent may be biostable and/or bioabsorable. The terminology "drug" as used herein should be understood to refer to a variety of therapeutic and diagnostic agents. In a further aspect of the invention, the drug is intended to prevent or inhibit restenosis.

The balloon is heated by heating the mold using a heat transfer medium which provides temperature control to the mold with a tolerance of about ±1 degree to about ±2 degrees Fahrenheit (F.)). In still another aspect of the invention, heating the mold comprises submerging the mold in a liquid bath, or contacting the surface of the mold with a conductive heating element. As a result, the heat transfer medium heats the mold primarily by conduction, and provides for finer temperature control and quicker heating than is provided by heating methods which heat primarily by convection (e.g., heating with hot air). In contrast, heating with hot air provides a heating tolerance of about ±10 degrees. In a presently preferred embodiment, the heat transfer medium is a conductive heating element such as a platen (e.g., a heated flat metal plate) configured to provide uniform heating of the balloon within the mold when the platen is in contact with the mold. Thus, the temperature is uniform (i.e., within about ±2 degrees F.) along the length of the section of the mold exposed to the heating medium, and the temperature at any given point of the heated length remains constant (i.e., within ±2 degrees F.) during the heating. With the metal platen pressed against an outer surface of the mold, the platen heats purely by conduction (unlike a hot circulating heating medium which heats by both conduction and convention), and provides for finer temperature control at the surface of the mold than a hot liquid bath or hot air. The temperature control provided by the heat transfer medium prevents the drug from being exposed to an elevated temperature which is above the thermal limit of the drug, while allowing the balloon to be quickly heated to a sufficiently high temperature to soften the balloon material during stent mounting.

In still another aspect of the invention, in which the heat transfer medium is a hot liquid bath, the mold is configured to seal the bore of the mold with the catheter therein, so that the mold is submerged without liquid or humidity from the liquid bath contacting the drug delivery stent in the mold. As a result, the drug delivery layer is not dissolved or otherwise damaged by exposure when the mold is submerged in the liquid bath.

The metallic material of the mold allows the mold to be machined with tight dimensional tolerances, to provide an accurate and uniform bore diameter. Additionally, the metallic material of the mold provides sufficient strength, even at elevated temperature, so that the mold radially restrains the stent during the stent mounting procedure without the diameter of the mold bore increasing. Thus, unlike a radial restraining member which expands somewhat during pressurization of the balloon therein, the mold of the invention controls the outer diameter of the mounted stent, so that the profile of the mounted stent is not disadvantageously increased during the stent mounting. The profile of the mounted stent can impact the ability of the stent delivery balloon catheter to advance and cross tight lesions in the patient's vasculature.

In one aspect of the present invention, the mold may be a split-mold. The mold may have hinged halves. The mold halves swing open and close at the hinge so that the balloon with the stent thereon can be introduced or removed from the mold without damaging the drug delivery layer of the stent. The mold therefore prevents or inhibits the damage to the drug delivery layer which can otherwise occur with tubular radial restraining members which don't open up for introduction of the balloon catheter and which must be cut off the balloon catheter after the stent mounting. Additionally, the mold of the invention is reusable, and provides for accurate, uniform heating which does not vary with each subsequent use.

In another aspect of the invention, the mold body defining the entire length of the bore and outer surface of the mold is formed of metal. As a result, the metal mold substantially uniformly heats the entire length of the balloon within the bore of the mold. However, in yet another aspect of the invention, the mold has a body with a heat conducting metallic section and an insulating non-metal section, so that heating the mold selectively heats sections of the balloon within the bore of the mold. The insulating section of the mold insulates the drug-delivery stent during the stent mounting procedure, so that the drug delivery stent is heated to a lower temperature than the inflatable sections of the balloon at either end of the stent. As a result, the balloon is sufficiently heated for the stent mounting procedure without exposing the drug-delivery stent to a disadvantageously high temperature (e.g., a temperature above the thermal limit of the drug).

A stent delivery balloon catheter of the invention generally comprises an elongated shaft having an inflation lumen and a guidewire lumen, a balloon on a distal shaft section having an interior in fluid communication with the inflation lumen, and a stent releasably mounted on the balloon for delivery and deployment within a patient's body lumen. The stent typically comprises an open-walled body of stent struts with gaps between adjacent struts. The balloon typically has a folded noninflated configuration with wings wrapped around the circumference of the balloon. In alternative embodiments, the balloon is a wingless balloon which expands by stretching from a wingless noninflated configuration.

Yet another aspect of the invention is directed to a mold having a stepped inner diameter comprising enlarged inner diameter sections on either end of a middle section. During stent mounting, the stepped inner diameter forms one or more external shoulders in the balloon. The balloon shoulders are located adjacent the end(s) of the stent, to prevent or inhibit the stent from moving longitudinally relative the balloon during delivery and deployment of the stent. The balloon external shoulders have an outer diameter larger than the outer diameter of the unexpanded stent, and thus provide a barrier that the stent would have to overcome in order to move longitudinally relative to the balloon. The external shoulders are thus molded into the balloon material during stent mounting and are not the result of material added to the shaft or balloon. As a result, the shoulders are formed without affecting the stiffness transitions of the catheter.

Another aspect of the invention is directed to a method of mounting a stent on a stent delivery balloon catheter using the mold having a stepped inner diameter. The method generally comprises introducing inflation media into the interior of the balloon, and heating the balloon, to radially expand the balloon with the stent restrained from radially expanding by a mold around an outer surface of the stent, so that the balloon expands into the stent gaps to embed the stent in an outer surface of the balloon, to thereby mount the stent on the balloon, wherein the mold has a stepped inner diameter so that expanding the balloon forms at least one shoulder in the balloon adjacent an end of the stent with an outer diameter greater than an outer diameter of the mounted stent in an unexpanded configuration.

In one aspect, the invention provides a method of mounting a drug delivery stent on a catheter balloon which provides a low profile mounted stent, and which securely and consistently mounts the stent on the balloon for delivery and deployment within a patient's body lumen without damaging the drug delivery layer of the stent. The metallic mold, heated primarily by conduction during stent mounting, allows temperature control to the mold sufficient to prevent heat damage of the drug delivery layer. The mold is heated with a method configured to avoid the nonuniformity and irreproducibility of convective heat transfer. Additionally, the mold is configured to prevent or reduce roughening or otherwise mechanically damaging the drug delivery layer, so that the drug delivery layer release rate and drug amount are not disadvantageously effected by the stent mounting procedure of the invention. In still another aspect of the invention, the mold has heat conducting portions and insulating portions, and heating the mold selectively heats sections of the balloon and stent within the bore of the mold. In yet another aspect of the invention directed to a mold with a stepped inner diameter, the mold produces one or more shoulders in the balloon which enhance stent retention on the balloon.

In yet one further aspect of the present invention, the method may further including re-crimping the catheter assembly after removal from the split mold. Re-crimping may be done by hand, hand tool, or using a crimping tool or machine. In one aspect of the invention, the re-crimping is performed using an MSI crimper available from Machine Solutions Incorporated, Flagstaff Ariz. In yet another aspect of the invention, the re-crimping may be performed using a stent press machine available from Advanced Cardiovascular Systems, Inc., Santa Clara, Calif.

In still another aspect of the invention, during the re-crimping process, the balloons may be pressurized and heated to increase the protrusion of balloon material into the openings in the stent pattern, thereby further increasing stent retention on the balloons. In one aspect of the invention, the balloon may be pressurized in the range of 10 to 300 pounds per square inch (psi) (7 to 207 newtons per square centimeter). In one aspect of the invention, the balloon and the mounted stent are heated to the range of about 100 degrees to 250 degrees Fahrenheit (38 to 121 degrees Celsius) during re-crimping. In yet another aspect of the invention, the mounted stent is heated to about 130 degrees Fahrenheit (54 degrees Celsius) during re-crimping. In another aspect of the invention, the balloon may be pressurized from about 10 psi (7 newtons per square centimeter) to about 70 psi (48 newtons per sq. centimeter). In yet a further aspect of the invention, the balloon may be pressurized to more or less pressure.

Re-crimping may increase the retention of the stent to the balloon, particularly if the catheter assembly is to be gas sterilized with ethylene oxide (EtO). In one aspect of the invention, the method includes a first stage of crimping the stent on the balloon catheter assembly before sterilization. The crimping before sterilization may be performed using any presently available crimping machine or crimping assembly. A crimping assembly may also be referred to sometimes as a crimping press. In yet a further aspect of the invention, after the first stage of crimping, the balloon is pressurized and heated within the mold to further mount the stent on the balloon. In still another aspect of the invention, a second crimping of the stent on the balloon catheter assembly is performed after removal from the mold, hereinafter also referred to as re-crimping.

In one aspect of the present invention, the method includes re-crimping the catheter assembly after removal from a split mold process. During the split mold process, pressure is applied to the balloon, and heat is applied to the balloon-stent assembly. It is after the split mold process that the balloon is likely to pull away from the stent, especially after EtO sterilization. Re-crimping is advantageous in securing the stent onto the balloon after the split mold process and when sterilization is accomplished by EtO sterilization. Re-crimping may also be advantageous in securing the stent onto the balloon after the split mold process when other sterilization methods are used.

In accordance with certain aspects of the present invention there may be provided a stent crimping assembly as disclosed in U.S. Pat. No. 6,840,081 filed Nov. 18, 2002 and entitled "ASSEMBLY FOR CRIMPING AN INTRALUMINAL DEVICE OR MEASURING THE RADIAL STRENGTH OF THE INTRALUMINAL DEVICE AND METHOD OF USE" which issued Jan. 11, 2005, the entire contents of which are incorporated herein by reference.

In further accordance with the present invention, there may be provided a stent crimping assembly as disclosed in U.S. Ser. No. 10/330,016 filed Dec. 26, 2002 and entitled "ASSEMBLY FOR CRIMPING AN INTRALUMINAL DEVICE AND METHOD OF USE" the entire contents of which are incorporated herein by reference.

One aspect of the present invention is a method of mounting a stent on a balloon catheter, including positioning the stent on a balloon of the balloon catheter and applying a first radially compressive force on an outer surface of the stent, thereby decreasing the outer diameter of the stent on the balloon catheter. The method also includes pressurizing and heating the balloon while restricting radial expansion of the outer surface of the stent. Yet a further aspect of the invention includes applying a second radially compressive force on the outer surface of the stent.

At least one aspect of the invention is a method of mounting a stent on a balloon catheter. The method includes positioning a stent on a balloon catheter, the balloon catheter having an elongated shaft with an inflation lumen and a guidewire lumen and an inflatable balloon on a distal shaft section with an interior in fluid communication with the inflation lumen. The stent has an open-walled body of stent struts with gaps between adjacent stent struts. The method further includes applying a first radially compressive force on an outer surface of the stent and thereby decreasing the outer diameter of the stent on the balloon catheter. In yet another aspect, the invention includes heating the balloon and introducing inflation media into the interior of the balloon to radially expand the balloon with the stent restrained from radially expanding, so that the balloon expands into the stent gaps to embed the stent in an outer surface of the balloon, and thereby mount the stent on the balloon. In at least one aspect of the invention, the stent is restrained from radially expanding by a mold. In yet one other aspect of the invention, the method includes removing the inflation media from the balloon interior and applying a second radially compressive force on an outer surface of the stent. In at least another aspect of the invention, one factor in increased retention of the stent on the balloon is that the second radially compressive force decreases the outer diameter of the stent on the balloon catheter.

Still another aspect of the invention is a method of increasing retention of an intravascular device on a balloon catheter, including a first stage of crimping the intravascular device onto a balloon of the balloon catheter, a second stage of heating and pressurizing the balloon, and a third stage of re-crimping the intravascular device onto the balloon of the balloon catheter.

Other features and advantages of the invention will become more apparent from the following detailed description of preferred embodiments of the invention, when taken in conjunction with the accompanying exemplary drawings.

BRIEF DESCRIPTION OF THE DRAWINGS

FIG. 1 is an isometric view of a mold useful in a method which embodies features of the invention, in which a drug delivery stent is mounted onto a balloon catheter.

FIG. 2 is an isometric view of the mold of FIG. 1 in a closed configuration, illustrating a distal section of a balloon catheter within the mold.

FIG. 3 is a longitudinal cross sectional view illustrating the mold of FIG. 2 with heating platens on an outer surface of the mold during a method of mounting a drug delivery stent on the balloon of the balloon catheter.

DETAILED DESCRIPTION OF THE PREFERRED EMBODIMENTS

FIG. 1 illustrates a metal mold 10 useful in a method of mounting a drug delivery stent on a balloon catheter, embodying features of the invention. Mold 10 generally comprises a split metal body 11 with a bottom half, a top half, and a polished bore 12 configured to receive a balloon catheter therein. In the embodiment illustrated in FIG. 1, the top and bottom halves of the mold are joined by a hinge, and the mold is illustrated in an open configuration. FIG. 2 illustrates the mold in a closed configuration with a distal section of a balloon catheter 20 in position within the mold.

Figure 4:
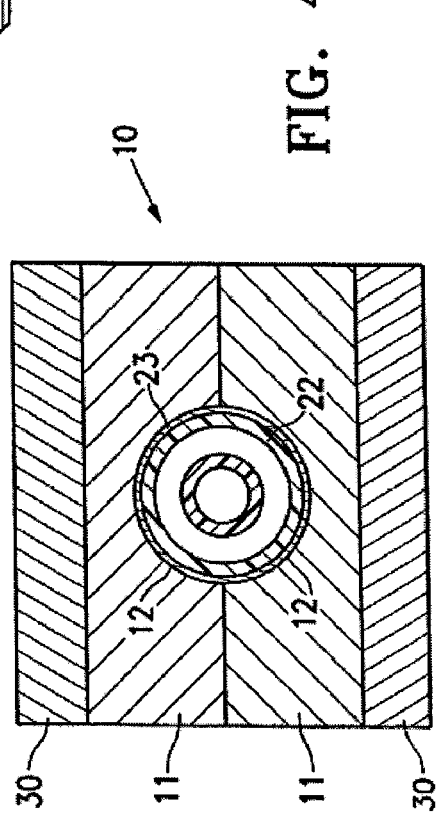
FIG. 4 is a diagrammatic transverse cross section of the assembly of FIG. 3, taken along line 4-4.

FIG. 3 illustrates the mold 10 with the distal section of the balloon catheter 20 therein, partially in longitudinal cross section, during a method of mounting a drug delivery stent on the balloon catheter 20. The balloon catheter 20 has an elongated shaft 21 with a balloon 22 on a distal section thereof and a drug delivery stent 23 on the balloon. The balloon 22, with the drug delivery stent 23 thereon, are completely contained within the polished bore 12 of the mold 10. FIG. 4 illustrates a diagrammatic transverse cross sectional view of FIG. 3, taken along line 4-4.

Figure 5:
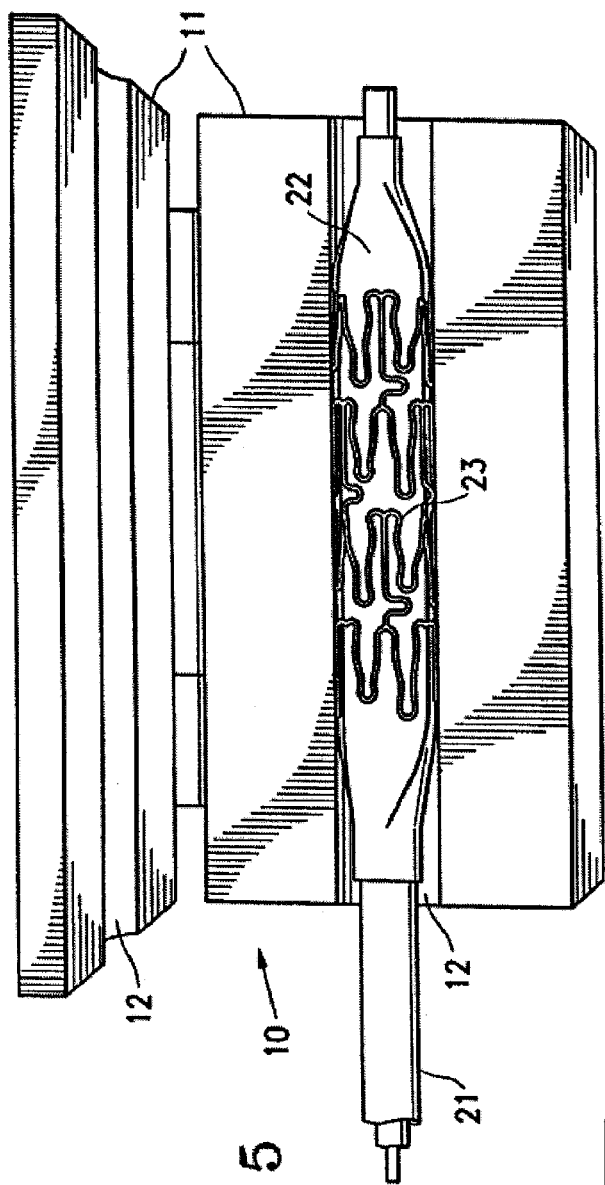
FIG. 5 is a perspective view of the mold of FIG. 3 in an open configuration allowing for removal from the mold of the stent delivery balloon catheter having the drug delivery stent mounted on the balloon.

A method of releasably mounting the drug delivery stent 23 on the balloon 22 generally comprises positioning the drug delivery stent 23 on the uninflated balloon 22 of the balloon catheter 20. The stent is typically mechanically crimped (i.e., radially collapsed) down onto the balloon 22. A distal end section of the catheter 20 is placed within the mold, to position the balloon with the crimped stent 23 thereon within the polished bore 12 of the mold 10. In one embodiment, the mold is a split-mold with hinged halves. The hinged halves of the mold are closed together, and the balloon 22 is pressurized by introducing inflation fluid into the interior of the balloon 22 and heated to an elevated temperature. In a presently preferred embodiment, the balloon is pressurized and then heated in the pressurized condition. In an alternative embodiment, the balloon is simultaneously pressurized and heated. The balloon material at the elevated temperature and pressure is forced into the gaps in the wall of the stent 23, to embed the stent within the outer surface of the balloon. FIG. 3 illustrates the balloon in the pressurized and heated state, with the stent contacting the polished inner surface of the bore of the mold to radially restrain the stent from radially expanding. In one embodiment, the balloon is pressurized to a relatively high pressure of about 15 to about 23 atm, more specifically about 19 to about 21 atm. The balloon is then cooled in the mold prior to depressurization of the balloon, and the cooled balloon depressurized, and the balloon catheter removed from the mold with the stent mounted on the balloon. FIG. 5 illustrates the mold 10 in an open configuration facilitating removal of the balloon catheter 20 therefrom after the stent 23 is mounted onto the balloon 22.

The mold bore 12 is defined by a polished inner surface of the top and bottom halves of the mold. In a presently preferred embodiment, the polished inner surface has a polish finish of about 0.4 microns or less. The bore is polished by techniques known in the art, such as honing. The polished inner surface contacts the stent, and provides a smooth surface which prevents or inhibits roughening the surface of the drug delivery stent 23 during the stent mounting procedure.

In the embodiment illustrated in FIGS. 1-5, the diameter of the bore 12 is the same along the entire length of the mold 10. The bore 12 is preferably formed by machining so that the diameter of the bore is highly accurate and uniform (i.e., the diameter varies by no more than ±0.025 mm along the length of the mold, and multiple molds can be made having the same dimensions). The bore 12 is preferably machined within the block which forms the body of the mold 10, with the two halves of the mold 10 in place together during the machining. As a result, the top and bottom sections of the bore 12 perfectly and repeatably mate together when the two halves of the mold 10 are closed together. In a presently preferred embodiment, the diameter of the mold bore 12 is slightly larger than the outer diameter of the crimped stent 23 on the balloon 22. As a result, the diameter of the mold bore 12 is large enough to avoid scuffing/damaging the drug delivery layer of the stent 23 when the balloon 22 and stent 23 crimped thereon are placed within the bore 12. In an alternative embodiment, the diameter of the mold bore 12 is equal to the diameter of the crimped stent 23 on the balloon 22, so that the stent does not radially expand during the stent mounting. Each half of the mold 10 preferably has relatively thin walls, e.g., with a wall thickness of not greater than about 0.25 to about 0.5 mm, at its thinnest along a midline of the bore 12 of the mold (i.e., the wall thickness from the outer surface of the mold half to the bore), to provide fast heating and cooling within the bore 12 of the mold 10.

In accordance with the invention, the balloon 22 is heated by heating the mold 10 with a heat transfer medium which provides very accurate temperature control to the mold 10. In the embodiment illustrated in FIG. 3, the heat transfer medium is a conductive heating element member in the form of metal platens 30. The metal platens 30 have a heating element (not shown) such as a resistive heater which heats the metal of the platens, and an inner surface typically configured to correspond to the outer surface of the mold 10. In the illustrated embodiment, the inner surface of the platens 30 and the outer surface of the mold 10 are flat, although, in alternative embodiments (not shown), the surfaces have irregular mating surfaces designed to increase the surface area thereof. The temperature at the surface of the platens 30 is very accurately controllable, so that, with the surface of the metal platens 30 pressed against the outer surface of the mold 10, the temperature of the mold can be very accurately controlled (i.e., with a tolerance which is not larger than about ±2 degrees F., more preferably with a tolerance of about ±1 degree F.).

With the balloon catheter 20 in position within the bore 12 of the mold 10, the mold 10 is slid into the space between the metal platens 30, and the metal platens 30 brought into contact with the outer surface of the top and bottom halves of the mold, to thereby heat the mold 10. The mold 10 is heated to an elevated temperature sufficient to soften the balloon 22 but lower than the thermal limit of the drug of the drug delivery stent 23. In a presently preferred embodiment, the temperature within the mold 10 is below a temperature which would cause the drug delivery layer of the stent 23 to flow. However, in an alternative embodiment in which the drug delivery layer of stent 23 is heated and flows somewhat at the elevated temperature, the smooth inner surface of the polished bore 12 causes the drug delivery layer to remain uniform in thickness without a roughened or irregular exterior. In one embodiment, the mold 10 is heated to a temperature of about 160° F. to about 190° F., with the balloon catheter 20 therein during the stent mounting procedure, to soften a balloon formed of polymeric material.

The metal platens 30 have a relatively high thermal conductivity, higher than that of air at least in the temperature range of interest, providing a relatively fast rate of heating. In one embodiment, the mold 10 is in contact with the heating platens 30 for not greater than about 120 seconds, and more specifically for about 60 to about 120 seconds during the stent mounting procedure. In contrast, hot air would take significantly longer, and for example not less than about 120 seconds (e.g., on the order of about 120 to about 240 seconds), to heat the mold to the desired temperature. The platens 30 and mold 10 are configured to provide a fast heating rate in combination with fine control of the elevated temperature, for improved mounting of the drug delivery stent 23 without damage to the drug delivery layer.

The platens 30 have a length which, in one embodiment, is at least as long as the stent 23, and the platens are brought into contact with a length of the mold 10 corresponding to the location of the drug delivery stent 23 therein. In the embodiment illustrated in FIG. 3, the platens are longer than the stent but shorter than the balloon, although a variety of suitable configurations can be used including platens having a length which is shorter than the stent, or platens having a length equal to the length of the mold 10. In a presently preferred embodiment, the platens have a length which is at least as long as, or substantially equal to, the length of the inflatable section of the balloon (i.e., the working length and tapered sections). Although discussed primarily in terms of the embodiment in which the mold is heated with platens 30, alternative heating mediums that heat primarily by conduction can be used including a hot liquid bath. In the embodiment using a hot liquid bath (not shown), the mold 10 has seals (not shown) at either end of the mold which seal around the balloon catheter 20 to prevent the liquid or humidity of the hot liquid bath from contacting the drug delivery stent 23 within the mold 10 when the mold is submerged within the bath.

Figure 6:
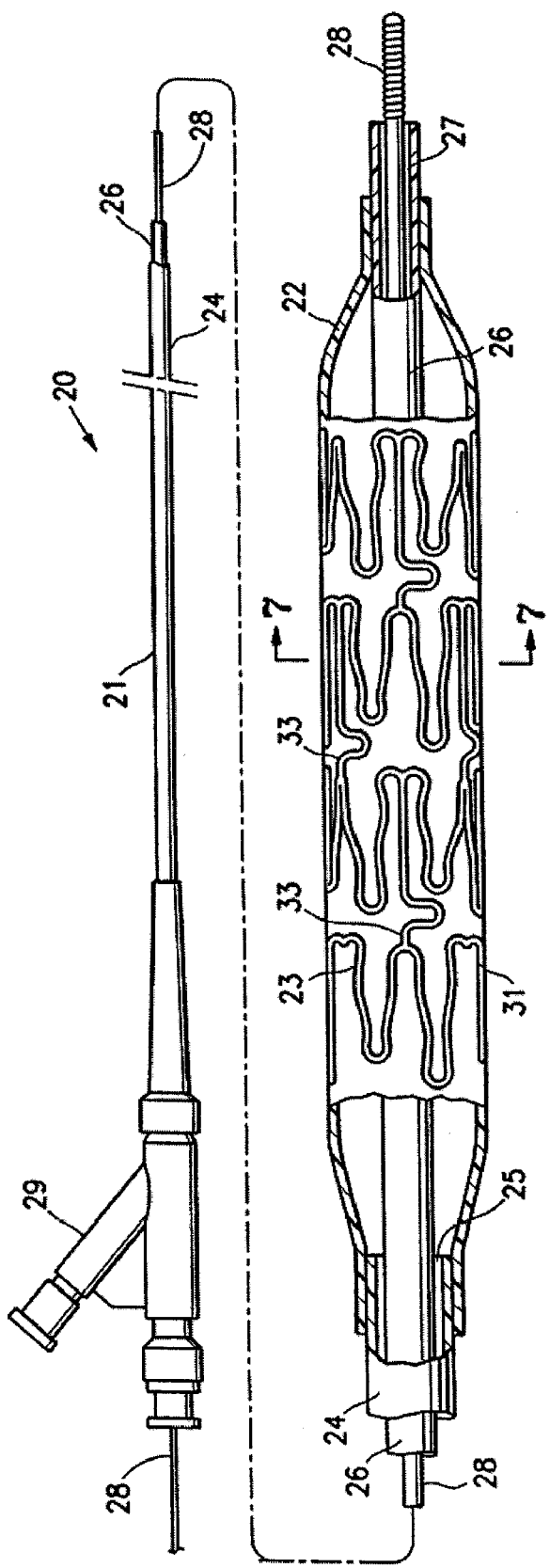
FIG. 6 is an elevational view of the stent delivery balloon catheter of FIG. 5 after being removed from the mold.
Figure 7:
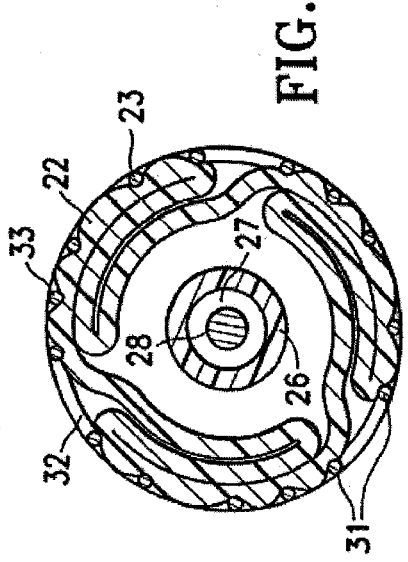
FIG. 7 is a transverse cross sectional view of the stent delivery balloon catheter of FIG. 6, taken along line 7-7.

FIG. 6 illustrates the stent delivery balloon catheter 20 embodying features of the invention, after removal from the mold 10 with the drug delivery stent 23 mounted on the balloon 22. In the illustrated embodiment, the catheter shaft 21 comprises an outer tubular member 24 defining an inflation lumen 25 therein, and an inner tubular member 26 defining a guidewire lumen 27 therein configured to slidingly receive a guidewire 28. Specifically, in the illustrated embodiment, the coaxial relationship between outer tubular member 24 and inner tubular member 26 defines annular inflation lumen 25. In the embodiment illustrated in FIG. 6, the guidewire lumen 27 extends to the proximal end of the catheter. Inflatable balloon 22 has a proximal skirt section sealingly secured to the distal end of outer tubular member 24 and a distal skirt section sealingly secured to the distal end of inner tubular member 26, so that the balloon interior is in fluid communication with inflation lumen 25. An adapter 29 at the proximal end of catheter shaft 21 is configured to provide access to guidewire lumen 27, and to direct inflation fluid through the arm into inflation lumen 25. As best shown in FIG. 7 illustrating a transverse cross section of the balloon catheter of FIG. 6, taken along line 7-7, the stent gaps are partially filled by the balloon material so that the balloon material contacts and partially encapsulates the side surfaces of the stent struts, to securely mount the stent on the balloon. In an alternative embodiment (not shown), the balloon material completely fills the stent gaps to fully encapsulate the side surfaces of the stent struts. In the embodiment illustrated in FIGS. 6 and 7 the portions of the balloon which protrude between the stent struts have an outer surface flush with the outer surface of the stent.

FIG. 6 illustrates the balloon 22, in a folded configuration with wings wrapped around the circumference of the balloon prior to complete inflation of the balloon. The balloon 22 typically has two or more, and most preferably three wings in the noninflated configuration, which unwrap during inflation of the balloon 22. For ease of illustration, a substantial gap is illustrated between the inner surface of the inflatable balloon interior and the shaft inner tubular member 26 in FIGS. 6 and 7, although it should be understood that the noninflated balloon is typically collapsed down around to inner tubular member in the noninflated configuration. The balloon expands to a generally cylindrical inflated configuration with a central working length inflated section, a proximal inflated conical tapered section proximal to the stent (and distal to the proximal skirt section), and a distal inflated conical tapered section distal to the stent (and proximal to the distal skirt section). FIG. 6 illustrates the stent 23 mounted on the central, working length section of the balloon 22, prior to complete expansion. The distal end of catheter 20 may be advanced to a desired region of the patient's body lumen in a conventional manner with the balloon in the noninflated configuration, and the balloon 22 inflated by directing inflation fluid into the balloon interior to expand the stent 23. The balloon is then deflated, leaving the drug delivery stent 23 implanted in the body lumen.

The stent 23 generally comprises an open-walled tubular body of interconnected, spaced-apart stent struts 31 with gaps 32 between adjacent stent struts. In the illustrated embodiment, the stent struts 31 form rings which have a serpentine wave pattern of opposed turns and which are longitudinally spaced apart and connected by links 33. However, the stent 23 can have a variety of suitable configurations as are conventionally known. The tubular body of the stent 23 is typically a biostable material such as a metal, although it can alternatively be formed of a bioabsorable material. In a presently preferred embodiment, the drug delivery layer is a coating (not shown) applied to the surface of the tubular body of the stent 23.

Although the embodiment illustrated in FIG. 6 is directed to embedding the drug delivery stent 23 in the outer surface of the layer of a single-layered balloon, it should be understood that the balloon can alternatively be formed of multiple layers or with an outer sleeve member, so that embedding the stent into the balloon embeds the stent in the outer surface of the outer most layer or outer sleeve of the balloon.

Figure 8:
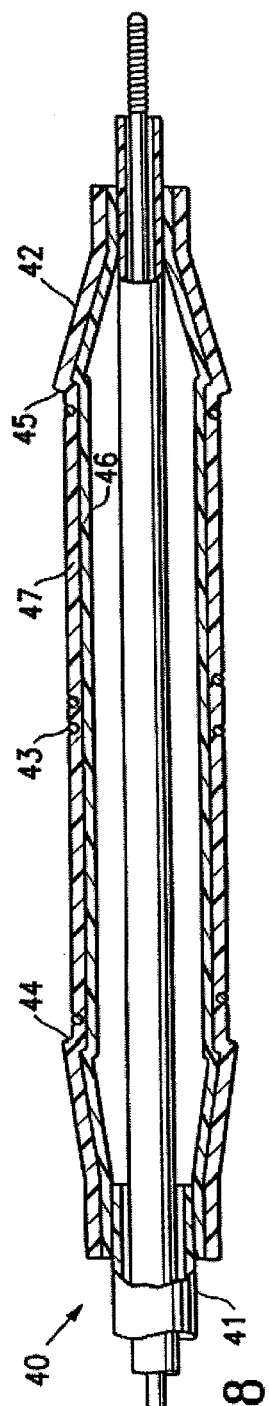
FIG. 8 illustrates a stent delivery balloon catheter embodying features of the invention, in which the balloon forms shoulders adjacent the ends of the stent.

FIG. 8 illustrates an alternative embodiment of a stent delivery balloon catheter 40 embodying features of the invention, having an elongated shaft 41 and a balloon 42 on a distal shaft section with a proximal external shoulder 44 adjacent a proximal end of the stent 43 with an outer diameter larger than the outer diameter of the nonexpanded stent mounted on the balloon, and a distal external shoulder 45 adjacent a distal end of the stent 43 with an outer diameter larger than the outer diameter of the nonexpanded stent mounted on the balloon. Alternatively, the balloon can have only one of the proximal 44 or distal 45 external shoulders. For example, in one embodiment (not shown), the balloon has the distal external shoulder 45, and not the proximal external shoulder 44. The external shoulders 44, 45 are located along the proximal and distal inflatable sections of the balloon (e.g., along the sections of the balloon which inflate to form the proximal and distal conical tapered sections in the inflated configuration, at the junction between the inflatable conical tapered section of the balloon and the end of the working length section). The stent 43 is similar to drug delivery stent 23 discussed above in relation to the embodiment of FIG. 1.

In the illustrated embodiment, the balloon 42 comprises an inner layer 46 and an outer sleeve member 47 which defines the outer surface of the external shoulders 44, 45. The outer sleeve 47 is typically formed of a relatively low melting point elastomeric polymer. In the embodiment illustrated in FIG. 8, molding the external shoulders 44, 45 in the outer sleeve 47 of the balloon also forms shoulders in the balloon inner layer 46.

The balloon 42 is illustrated in a partially inflated configuration in FIG. 8 for ease of illustration, but it should be understood that the working length of the balloon is typically collapsed down to the shaft inner tubular member in the noninflated configuration for advancement within the patient's body lumen. In one embodiment, the balloon inflates to a cylindrical, fully inflated configuration (i.e., with no shoulders 44, 45 in the outer surface of the expanded balloon). The shoulders 44, 45 thus substantially disappear as the balloon expands, with the working length of the balloon expanding to define the maximum inflated diameter of the balloon, and the conical sections on either end of the working length section tapering away from the working length section to a smaller outer diameter in the inflated configuration.

Figure 9:
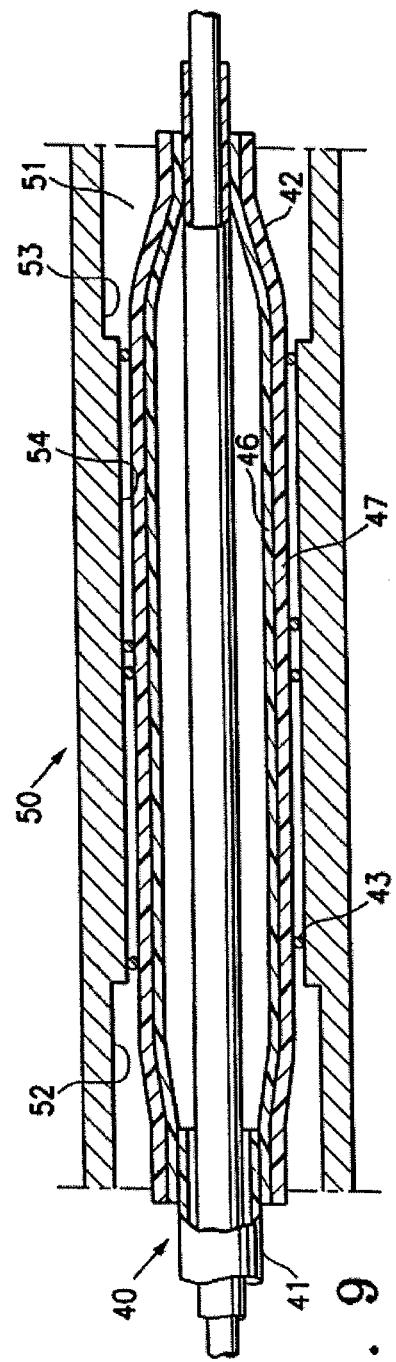
FIG. 9 illustrates a mold useful in a method of mounting a stent on a balloon catheter, having a stepped inner diameter, to form the shoulders in the balloon.

In a method of mounting the stent 43 on the balloon catheter 40 to form the stent delivery system of FIG. 8, the radial restraining mold 50 has a stepped inner diameter which forms the external shoulders 44, 45 in the balloon during the stent gripping. FIG. 9 illustrates balloon catheter 40 within a radial restraining mold 50 having an inner chamber 51 configured for receiving the balloon portion of the balloon catheter 40. The radial restraining mold 50, similar to the embodiment of FIG. 1, typically has a bottom half attached by hinges to a top half, which facilitates positioning the balloon portion of the catheter in the inner chamber 51 of the mold. The inner chamber 51 has enlarged inner diameter sections 52 and 53 on either end of a middle section 54. The balloon is illustrated with the outer sleeve 47 and stent 43 thereon, during pressurization of the balloon to mount the stent on the balloon. As set forth above, the mold 50 radially restrains the stent 43 as inflation media is introduced into the interior of the balloon and the mold is heated to heat the balloon, so that the balloon expands into the stent gaps and the external shoulders 44, 45 are formed in the balloon by the enlarged inner diameter sections 52, 53 of the mold 50. In the embodiment illustrated in FIG. 8, the inner surface of the balloon also has a stepped configuration at the shoulders. As a result, a gap exists between the inner surface of the balloon at the shoulders 44, 45 and the outer surface of the shaft (or the outer surface of a radiopaque marker (not shown) on the shaft if the radiopaque marker is located beyond the end of the stent) in the noninflated configuration. Although the embodiment illustrated in FIGS. 8 and 9 has the outer sleeve 47 on the balloon inner layer 46, it should be understood that in an alternative embodiment (not shown) the outer sleeve 47 is omitted. The method fully or partially embeds the stent 43 in the balloon 42 depending on the balloon material and stent mounting method conditions.

Figure 10:
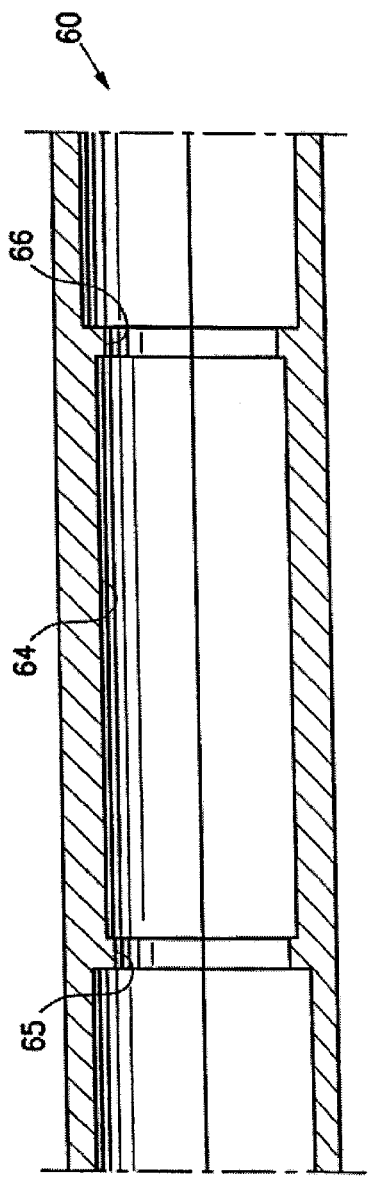
FIG. 10 illustrates a longitudinal cross sectional view of an alternative embodiment of a stepped inner diameter mold useful in a method of mounting a stent on a balloon catheter, in which end portions of the middle section of the mold have a smaller inner diameter than the portion of middle section therebetween.

FIG. 10 illustrates a longitudinal cross sectional view of an alternative radial restraining mold 60 with a stepped inner diameter, in which end portions 65, 66 of the middle section 64 of the mold have a smaller inner diameter than the portion of middle section 64 therebetween. The reduced inner diameter end portions 65, 66, cause the ends of the stent 30 to further embed down into the balloon during the stent mounting. Embedding the ends of the stent to a greater degree than a central section of the stent improves stent retention and advanceability of the system.

Figure 11:
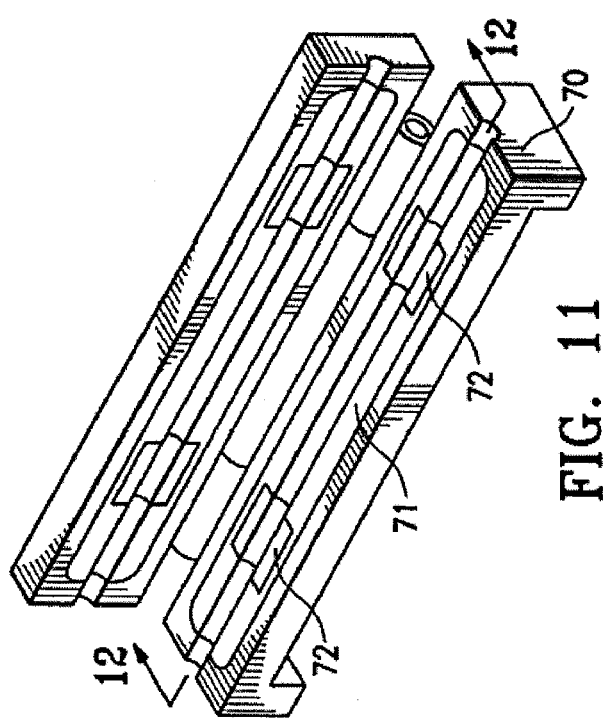
FIG. 11 is an isometric view of an alternative mold useful in a method embodying features of the invention, having an insulating non-metal body portion and a metal body portion.

In a presently preferred embodiment, the mold 10/50/60 is formed of metal, so that the metallic body of the mold defines the entire length of the bore that receives the balloon, and defines an outer surface of the mold. The metallic body substantially uniformly heats the entire length of the balloon within the mold. In an alternative embodiment, the mold selectively heats sections of the balloon within the bore of the mold (i.e., the mold has sections which differentially conduct heat). For example, FIG. 11 illustrates an isometric view of an alternative radial restraining mold 70, having a body 71 formed of an insulating material such as a plastic with metal portions 72, which allows for selective heating of the balloon portion of a catheter. The metal portions 72 are heat conducting, and the insulating (e.g., plastic) body 71 is not heat conducting, or at least is substantially less heat conducting than the metal portions. For example, when a metal portion was heated to 163° F. (73° C.), the maximum temperature measured in the adjacent insulating plastic portion was 109° F. (43° C.). As a result, the balloon portion proximal and distal to the stent can be placed at the metal portions 72, with the balloon central working length section (having the stent thereon) located between the metal portions 72, so that the plastic of the mold body insulates the working length section of the balloon portion from the elevated temperatures used during the stent mounting.

Insulating at least the central working length section of the balloon portion from heat protects the drug delivery coating of the stent from damage during the stent mounting procedure. Depending on the length of the metal portions 72, the plastic body 71 typically also insulates the balloon skirt sections (secured to the shaft) from heat of the heat transfer medium during the stent mounting procedure.

In a presently preferred embodiment, the insulating material forming the mold body 71 is a plastic such as polyetheretherketone (PEEK), or a machinable polyimide such as Vespel, although non-plastic insulating materials can alternatively be used such as ceramics including Macor (a machinable glass ceramic).

Figure 12:
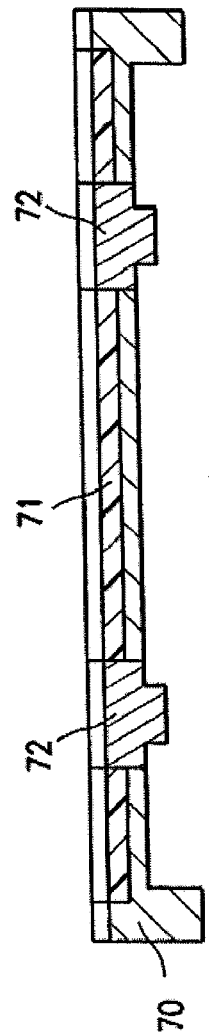
FIG. 12 illustrates a longitudinal cross sectional view of the mold bottom half of FIG. 11, taken along line 12-12.

FIG. 12 illustrates a longitudinal cross sectional view of the bottom half of the mold 70 of FIG. 11, taken along line 12-12. In a presently preferred embodiment, the metal portions 72 have, along at least a section thereof, a larger wall thickness (from the inner to the outer surface) than the adjacent sections of the plastic body 71 so that the metal portions 72 have at least a section which protrudes from the outer surface of the plastic body 71. The heating platens (discussed above in relation to the embodiment of FIG. 3) will therefore contact the protruding outer surface of the metal portions 72 without contacting the plastic body 71 during the stent mounting procedure. The air gap between the heating platens and the plastic body 71 sections will further reduce heat transfer to the drug delivery layer of a stent within the mold 70. In the illustrated embodiment, the plastic body 71, which together with the metal portions 72 defines the length of the bore receiving the balloon, is within an outer housing, typically formed of a metal, which surrounds the outer surfaces of the plastic body. The illustrated metal portions 72 have a section with a sufficiently large wall thickness such that the metal portions 72 protrude from the outer surface of the outer housing.

Figure 13:
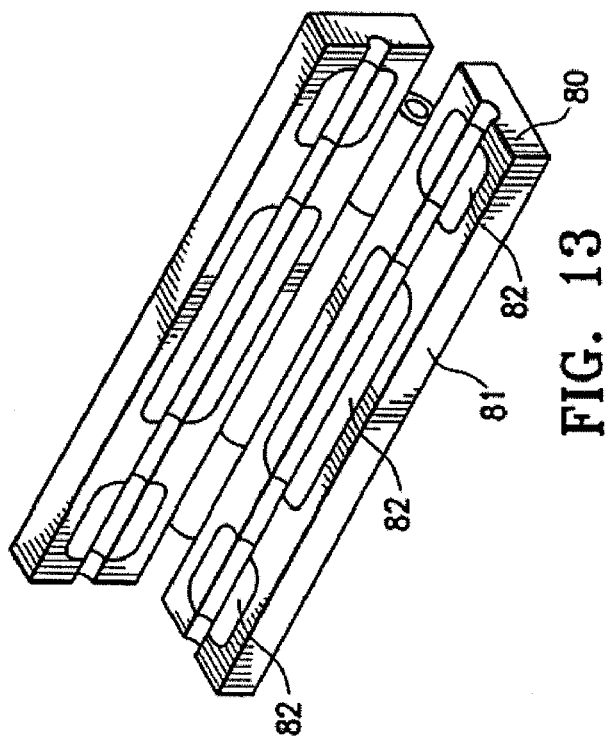
FIG. 13 is an isometric view of an alternative partially insulating mold useful in a method embodying features of the invention, having a metallic body with insulating non-metal inserts.

FIG. 13 illustrates an isometric view of an alternative embodiment of a selective heating mold 80 which embodies features of the invention, having a metallic body 81 with insulating plastic inserts 82. In the illustrated embodiment, three plastic inserts 82 are present, positioned at sections of the mold configured to receive the central working length section of balloon, and the skirt sections of the balloon secured to the shaft. The sections of the metallic body 81 of the mold located between the adjacent plastic inserts 82 are configured to receive the inflatable conical sections of the balloon (i.e., the balloon sections which extend between the central working length and the skirt sections of the balloon). The plastic inserts 82 preferably have a wall thickness which is less than the wall thickness of the metallic body 81. As a result, the metallic body 81 preferably defines the outer surface of the mold along the entire length thereof, and the metallic body 81 together with the plastic inserts 82 define sections of the bore of the mold. Alternatively, the wall thickness of the plastic inserts is equal to the wall thickness of the metallic body, so that the metallic body together with the plastic inserts define sections of the outer surface of the mold 80.

The dimensions of the stent delivery balloon catheter 20, 40 are determined largely by the size of the balloon and guidewire to be employed, the catheter type, and the size of the artery or other body lumen through which the catheter must pass or the size of the stent being delivered. Typically, the outer tubular member 24 has an outer diameter of about 0.025 to about 0.04 inch (0.064 to 0.10 cm), usually about 0.037 inch (0.094 cm), and the wall thickness of the outer tubular member 24 can vary from about 0.002 to about 0.008 inch (0.0051 to 0.02 cm), typically about 0.003 to 0.005 inch (0.0076 to 0.013 cm). The inner tubular member 26 typically has an inner diameter of about 0.01 to about 0.018 inch (0.025 to 0.046 cm), usually about 0.0+16 inch (0.04 cm), and a wall thickness of about 0.004 to about 0.008 inch (0.01 to 0.02 cm). The overall length of the catheter 20, 40 may range from about 100 to about 150 cm, and is typically about 143 cm. Preferably, balloon 22, 42 has a length of about 0.8 cm to about 6 cm, and an inflated working diameter of about 2 mm to about 10 mm.

Inner tubular member 26 and outer tubular member 24 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 6 is an over-the-wire type balloon catheter, the catheter of this invention may comprise a variety of intravascular catheters, such as rapid exchange type balloon catheters. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

The terms crimping and compressing as used herein are meant to be interchangeable and mean that the diameter of the stent is reduced to some degree. Typically, balloon-expandable stents 23 are known by persons having ordinary skill in the art to be "crimped" onto the balloon 22 portion of a catheter 20 while self-expanding stents are compressed onto a mandrel or sheath and then inserted into a catheter. The term re-crimping as used herein refers to a second radially compressive force on an outer surface of the stent following a first radially compressive force on an outer surface of the stent. The re-crimping may use the same crimping apparatus and/or method as the first crimping, or a different crimping apparatus and/or method. Both crimping and re-crimping include applying a radially compressive force on an outer surface of the stent and thereby decreasing the outer diameter of the stent on the balloon catheter. Re-crimping as used herein also refers to applying a radially compressive force on an outer surface of the stent after removal from the mold 10. The term pre-mounting as used herein refers to the stent being placed onto the catheter assembly and compressed before the stent mounted catheter is inserted into the crimping assembly for the first crimping process. In one embodiment, pre-mounting the stent onto the balloon of the catheter assembly includes compressing the stent onto the catheter with finger pressure before the stent mounted catheter is inserted into the crimping assembly.

Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

The crimping processes referred to herein may be performed using the crimping assembly or apparatus referred to above or any other acceptable stent crimping assembly, apparatus, or method known in the art. A crimping assembly or apparatus may also be referred to sometimes as a crimping press. In one embodiment of the invention, a stent crimping assembly is used to crimp an expandable stent 23 onto the balloon 22 portion of a balloon catheter 20, however, the invention can be used with self-expanding stents as well. Examples of stent assemblies that may be used to crimp an expandable stent onto a balloon catheter include a stent crimping assembly as disclosed in U.S. Pat. No. 6,840,081 filed Nov. 18, 2002 and entitled "ASSEMBLY FOR CRIMPING AN INTRALUMINAL DEVICE OR MEASURING THE RADIAL STRENGTH OF THE INTRALUMINAL DEVICE AND METHOD OF USE" which issued Jan. 11, 2005, the entire contents of which are incorporated herein by reference and/or a stent crimping assembly as disclosed in U.S. Ser. No. 10/330,016 filed Dec. 26, 2002 and entitled "ASSEMBLY FOR CRIMPING AN INTRALUMINAL DEVICE AND METHOD OF USE" the entire contents of which are incorporated herein by reference.

In at least one embodiment, the invention includes a method of mounting a stent 23 on a balloon catheter 20. The stent is positioned on the balloon catheter by hand or apparatus. In at least one embodiment, the stent is pre-mounted onto the balloon 22 of the balloon catheter by a slight compressive pressure, for example, hand pressure. After positioning of the stent on the balloon, a first radially compressive force is applied on an outer surface of the stent, thereby decreasing the outer diameter of the stent on the balloon catheter. After applying of the first radially compressive force, the balloon is pressurized and heated while restricting radial expansion of the outer surface of the stent. In one embodiment, the pressurizing and heating of the balloon is done in a mold, for example, a split mold, configured to restrict the radial expansion of the outer surface of the stent. During the pressurizing and heating, outpouchings of the balloon may extend between undulations of the stent, further securing the stent on the balloon. However, the balloon may pull away from the stent somewhat as the balloon cools. The pulling away of the balloon from the stent may be exaggerated during EtO sterilization. Therefore, at least one embodiment includes applying a second radially compressive force on the outer surface of the stent. The second radially compressive force may decrease the outer diameter of the stent on the balloon catheter, wherein the stent is more securely mounted on the balloon. The first and/or second radially compressive forces may be applied by hand, by hand tool, or by machine, for example, a crimping maching. In at least one further embodiment, the assembly including the stent and balloon catheter may then be sterilized, for example, by EtO sterilization.

In at least one embodiment, the invention includes a method of increasing stent 23 retention on a balloon catheter 20. In one embodiment, the method includes a first stage of crimping the stent onto the balloon catheter before placing the balloon catheter with the stent mounted thereon in the mold 10, and a second stage of crimping of the stent onto the balloon catheter after the split mold process, described elsewhere herein, and before sterilization of the stent and balloon catheter assembly.

In a further embodiment, the invention is a method of increasing retention of an intravascular device on a balloon catheter, including a first stage of crimping the intravascular device onto a balloon of the balloon catheter, a second stage of heating and pressurizing the balloon, and a third stage of re-crimping the intravascular device onto the balloon of the balloon catheter.

In another embodiment, after the first stage of crimping, the stent 23 crimped on the balloon 22 is submitted to the split mold process described in greater detail above. After the first stage of crimping and the split mold process, the undulating rings of the stent indent into the balloon 22 resulting in out pouching or pillowing of the balloon into the openings between the undulations of the stent. In yet another embodiment, heating of the balloon and introducing inflation media into the interior of the balloon radially expands the balloon. The stent is restrained from radially expanding, for example, by the mold around an outer surface of the stent. As the balloon radially expands under heat, the balloon expands into the stent gaps to embed the stent in an outer surface of the balloon, thereby mounting the stent on the balloon.

However, a loss of stent retention may occur if sterilization of the balloon catheter 20 with the stent mounted thereon is performed directly after the split mold process. The loss of stent retention typically occurs with EtO (ethylene oxide) sterilization. One factor in the loss of stent retention may be that the balloon shrinks and pulls away from the stent during the sterilization process. Yet another factor in the loss of stent retention may be that the balloon shrinks and pulls away from the stent as it cools after the split mold process.

In one embodiment of the invention, the method may include applying at least one radially compressive force on the outer surface of the stent 23 that has been mounted on the balloon catheter 20 after removal from the mold 10. The mold may be a split mold.

In one embodiment, the stent is pre-mounted on the balloon and positioned in the mold. After removal from the mold, a radially compressive force is applied on the outer surface of the stent before sterilization of the stent-balloon catheter assembly.

During the split mold process, pressure is applied to the balloon 22, and heat is applied to the balloon-stent assembly. It is after the split mold process that the balloon may pull away from the stent 23. Re-crimping is advantageous in securing the stent onto the balloon after removal from the mold 10. The advantage of re-crimping the stent onto the balloon catheter 20 is that the re-crimping may increase the retention of the stent to the balloon, particularly if the catheter assembly is to be gas sterilized with ethylene oxide (EtO). In at least one embodiment, the re-crimping is performed after the split mold process without another stage of crimping having been performed before the split mold process.

Re-crimping may be done by hand, using a crimping tool, a crimping machine, a crimping press, and/or a crimping assembly. In one preferred embodiment, the re-crimping is performed using an MSI crimper available from Machine Solutions Incorporated, Flagstaff Ariz. In one embodiment, the re-crimping may be performed using a stent press machine available from Advanced Cardiovascular Systems, Inc., Santa Clara, Calif.

In one embodiment, during the crimping and/or re-crimping process the balloon 22 may be pressurized and heated to increase the protrusion of balloon material into the openings in the stent 23 pattern, thereby further increasing stent retention on the balloon. In yet another embodiment of the invention, the balloon may be pressurized in the range of 10 to 300 pounds per square inch (psi) (7 to 207 newtons per square centimeter).

In at least one embodiment of the invention, the balloon 22 having the stent 23 mounted thereon is heated to the range of about 70 degrees to 250 degrees Fahrenheit (21 to 121 degrees Celsius) during re-crimping. In one embodiment the mounted stent is heated to about 130 degrees Fahrenheit (54 degrees Celsius) during re-crimping. In one embodiment, the balloon may be pressurized to about 70 psi (48 newtons per sq. centimeter). In other embodiments, the balloon may be pressurized to more or less pressure. In one embodiment, processing time during the re-crimping is in the range of one second to five minutes. In at least one embodiment, the processing time is approximately 10 seconds.

The split mold process described above may include applying heat and pressure to the balloon 22 and stent 23 mounted thereon, while restraining radially expansion of the stent, for a first period of time in order to deform the balloon so that it conforms to the contours of the stent. In one embodiment, the first period of time is a short period of time, for example, 1-2 minutes. Following the split mold process, the stent delivery system is EtO sterilized. During EtO sterilization, the stent delivery system loses approximately 25% of the stent retention force. From examination of photos and stent OD measurements, it appears that the balloon is relaxing and does not conform as strongly to the contours of the stent. This balloon relaxation is likely caused by strain recovery due to residual stresses in the balloon material as it is exposed to temperatures above the glass transition temperature of the balloon material during the EtO process (a heat and humidity cycle).

In at least one other embodiment, the balloon 22 and stent 23 mounted thereon are exposed to heat and pressure, while restraining radially expansion of the stent, for a second period of time. The intent of the process is to relax the polymer chains of the balloon in the "gripped" orientation, such that it reduces the tendency of the balloon to relax during sterilization. The higher the temperature, the less time that it will take for the balloon polymer to set in the desired orientation. This process could be used to provide dimensional stability to any polymer component that experiences strain recovery when exposed to downstream processing temperatures above the glass transition temperature of the polymer. In one embodiment, the balloon is pressurized to between about 1 pound per square inch (0.7 newtons per square centimeter) to about 500 pound per square inch (345 newtons per square centimeter) during at least one of the first time period or the second time period. In at least one embodiment, the balloon is pressurized to between about 5 (3.5 newtons per square centimeter) pound per square inch and 300 pound per square inch (207 newtons per square centimeter) during at least one of the first time period or the second time period. In at least one further embodiment, the balloon is pressurized to between about 300 pound per square inch (207 newtons per square centimeter) pound per square inch and about 900 pound per square inch (621 newtons per square centimeter) during at least one of the first time period or the second time period. This method is also useful for increasing retention of drug delivery stents.

In at least one embodiment, the balloon 22 and stent 23 mounted thereon may be constrained or restrained in a mold 10, for example the radial restraining mold 50, during the second period of time. In one embodiment, the mold is a split-mold. The split mold may have hinged halves. In another embodiment, the balloon 22 and stent 23 mounted thereon may be constrained or restrained in a sheath. In at least one embodiment, the sheath used to restrain expansion of the stent is a protective sheath, such as those known in the art, wherein the sheath is configured for protecting a stent mounted on a balloon during shipment. In one embodiment, the stent is restrained to a diameter close to the desired final stent outer diameter. In one embodiment, the final stent outer diameter is the desired outer diameter of the stent just prior to delivery of the stent into the vessel to be treated.

In one embodiment, the heating process during the first time period or the second time period could use heat provided from forced air convection. In another embodiment, the heating process during the first time period or the second time period could use heat provided by conduction through the mold 10, 50. In yet another embodiment, the heating process during the first time period or the second time period could use the heat provided from an oven.

In one embodiment, the heating process exposes the balloon 22 and/or stent 23 to temperatures equal to, slightly below, or slightly above the glass transition temperature (Tg) of the balloon. Humidity or a transient plasticizing agent such as alcohol, acetone or other solvent suitable to the particular balloon material may also be applied to the balloon to lower the Tg.

In one embodiment, the second time period has a duration of about 15 seconds to about 48 hours. In another embodiment, the second time period has a duration of about 5 minutes to about 48 hours. These time periods are by way of example, and longer or shorter time periods may be used for the second time period.

In one further embodiment, the balloon 22 and stent 23 mounted thereon may be cooled during a third time period. In at least one embodiment, the cooling process during the third time period may be controlled. The rate of cooling and the amount of cooling may be controlled. In yet another embodiment, the balloon should remain pressurized during the cooling process of the third time period. In one embodiment, the third time period of cooling follows the second time period of heat and pressure. In another embodiment, the third time period of cooling is performed following after the first time period of heat and pressure and is performed again after the second time period of heat and pressure.

In yet one further embodiment, the method of crimping the stent onto the balloon of the balloon catheter may include crimping the stent onto the balloon more than once. In one embodiment, the stent is crimped before the first time period of heat and pressure. In another embodiment, the stent is re-crimped at least once after the first period of heat and pressure. In still another embodiment, the stent is re-crimped after the second period of heat and pressure.

EXAMPLE

Figure 14:
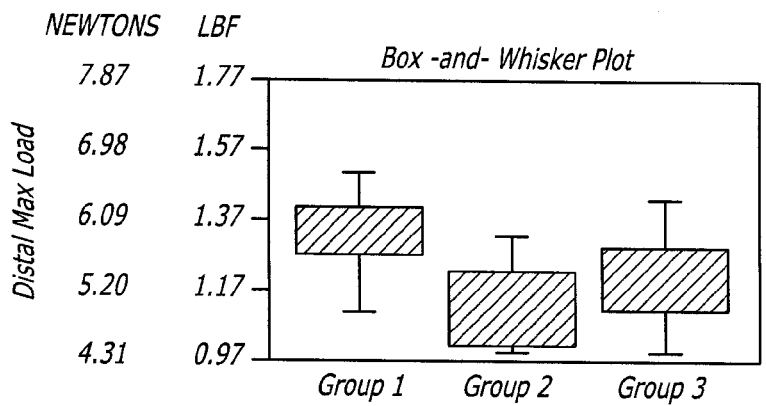
FIG. 14 is a box-and-whisker plot of dislodgement data for stents following EtO sterilization.
Figure 15:
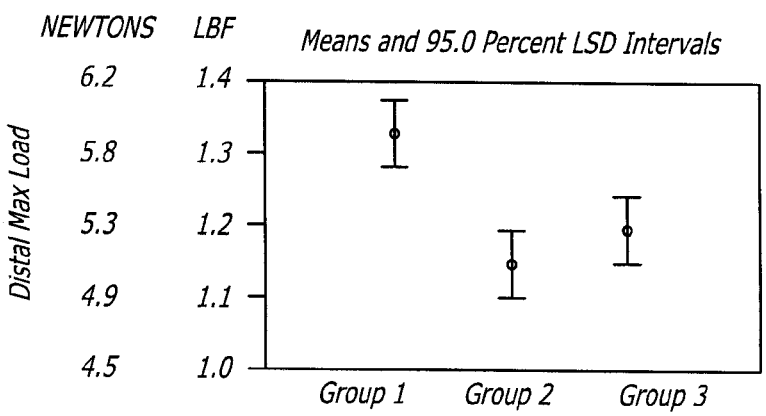
FIG. 15 which is a means plot of dislodgement data for stents following EtO sterilization.
Figure 16:
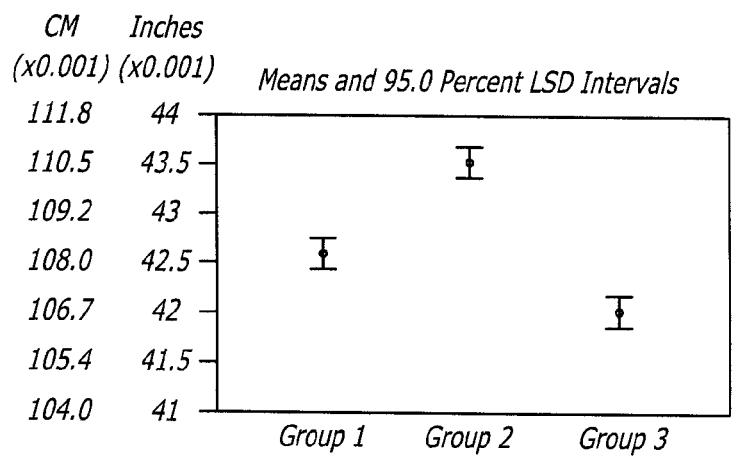
FIG. 16 is a plot of crimped stent O.D.

Referring now to FIGS. 14-16, balloon catheters 20 were divided into 3 groups. Sheaths configured for restraining radial expansion of the balloons and/or stents were placed over each of the balloons 22 with the stents 23 mounted thereon. In the first group, the balloons were pressurized to 30 psi (21 newtons per square centimeter). In the second group, the balloons were pressurized to 60 psi (41 newtons per square centimeter). The third group was a control group. The balloons of the catheters of the first and second groups were pressurized using standard airbox and stopcock. The pressurized balloon catheters with the stents mounted thereon were then placed in constant temperature oven set at 145° F. (63 degrees Celsius) for a duration of approximately 24 hours. This extended time was chosen to increase signal.

The balloon catheters 20 were then de-pressurized and packaged per normal operating procedures. The three test groups were then sent to EtO sterilization. All units were collected after EtO sterilization and submitted to the lab for randomized dislodgement testing.

The dislodgement results are shown in FIGS. 14-16. Referring now to FIG. 14 which is a box-and-whisker plot of the data, this plot shows that the spread of the data is not different between the three groups but does show that the first group has higher values and therefore better retention than the second and the third group. Referring now to FIG. 15 which is a means plot of the data, this plot shows that the dislodgement values for the first group are significantly higher at the 95% confidence level. However the second group was not significantly higher than the control and actually had a lower overall average retention.

Crimped stent data was also gathered as part of the test. The means plot for the average crimped stent OD (outer diameter) is shown in FIG. 16. This plot shows that the averaged crimped stent OD increases with increasing pressure with the first group averaging approximately 0.0006 inch larger than the control and the second group averaging approximately 0.0015 inch larger than the control with the differences between the groups being statistically significant at the 95% confidence level. The crimped stent OD (outer diameter) data was smaller than the ID (inner diameter) of the finished goods sheath. The deployment pressure for one kind of stent is around 60-75 psi (41-52 newtons per square centimeter).

The data shows that applying pressurized heat set to a stent 23 mounted on a balloon 22 does mitigate the loss of stent dislodgement force during EtO sterilization as long as the crimped stent OD is not significantly impacted. Pressurizing the system to a pressure where the stent actually begins to deploy results in no benefit to dislodgement from the pressurized heat set.

While the present invention is described herein in terms of certain preferred embodiments, those skilled in the art will recognize that various modifications and improvements may be made to the invention without departing from the scope thereof. For example, while discussed primarily in terms of a stent or a drug delivery stent, aspects of the invention may be useful with an alternative prosthesis or stent (e.g., a bare metal stent). Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A mold for mounting a stent on a balloon catheter, comprising:
   a mold having a first half and a mating second half and having a longitudinal bore having a constant bore diameter the length of the mold;
   the mold having a wall thickness in the range from 0.25 mm (0.00984 inch) to 0.50 mm (0.01969 inch); and
   the mold being formed from a first material and a second material, the second material being substantially less heat conducting than the first material.

2. The mold of claim 1, wherein the first material is a metal.

3. The mold of claim 2, wherein the second material is a non-metal.

4. The mold of claim 3, wherein the second material is formed from a polymer material.

5. The mold of claim 4, wherein the polymer material includes a polyetheretherketone or a machinable polyimide.

6. The mold of claim 3, wherein the second material is a ceramic.

7. The mold of claim 1, wherein the longitudinal bore has a metallic portion and a non-metallic portion.

8. The mold of claim 7, wherein the non-metallic portion of the longitudinal bore being substantially less heat conducting than the metallic portion of the longitudinal bore.

9. The mold of claim 7, wherein the non-metallic portion of the longitudinal bore being formed from a polymer material.

10. The mold of claim 9, wherein the polymer material includes a polyetheretherketone or a machinable polyimide.

11. The mold of claim 7, wherein the non-metallic portion of the longitudinal bore has a length that substantially corresponds to the length of the stent being mounted on the balloon catheter.

12. The mold of claim 7, wherein the metallic portion of the longitudinal bore has a length that substantially corresponds with a distal portion and a proximal portion of the balloon that extends beyond the length of the stent.

13. The mold of claim 1, wherein the first half of the mold is hinged to the second half.

14. A mold for mounting a stent on a balloon catheter, comprising:
   a mold having a first half and a second half and having a longitudinal bore having a constant bore diameter the length of the mold;
   the mold having a wall thickness in the range from 0.25 mm (0.00984 inch) to 0.50 mm (0.01969 inch); and
   the longitudinal bore being formed from a first material and a second material, the second material being substantially less heat conducting than the first material.

15. The mold of claim 14, wherein the first material is a metal.

16. The mold of claim 15, wherein the second material is a non-metal.

17. The mold of claim 16, wherein the second material is formed from a polymer material.

18. The mold of claim 17, wherein the polymer material includes a polyetheretherketone or a machinable polyimide.

19. The mold of claim 16, wherein the second material is a ceramic.

20. The mold of claim 16, wherein the non-metallic portion of the longitudinal bore has a length that substantially corresponds to the length of the stent being mounted on the balloon catheter.

21. The mold of claim 15, wherein the metallic portion of the longitudinal bore has a length that substantially corresponds with a distal portion and a proximal portion of the balloon that extends beyond the length of the stent.

* * * * *